(12) United States Patent
Smoot et al.

(10) Patent No.: US 10,416,754 B2
(45) Date of Patent: Sep. 17, 2019

(54) FLOOR SYSTEM PROVIDING OMNIDIRECTIONAL MOVEMENT OF A PERSON WALKING IN A VIRTUAL REALITY ENVIRONMENT

(71) Applicant: DISNEY ENTERPRISES, INC., Burbank, CA (US)

(72) Inventors: Lanny S. Smoot, Thousand Oaks, CA (US); Günter D. Niemeyer, Pasadena, CA (US); David Loyal Christensen, Glendale, CA (US); Robert Bristow, Burbank, CA (US)

(73) Assignee: DISNEY ENTERPRISES, INC., Burbank, CA (US)

( * ) Notice: Subject to any disclaimer, the term of this patent is extended or adjusted under 35 U.S.C. 154(b) by 142 days.

(21) Appl. No.: 15/790,124

(22) Filed: Oct. 23, 2017

(65) Prior Publication Data

US 2018/0217662 A1 Aug. 2, 2018

Related U.S. Application Data

(60) Provisional application No. 62/452,060, filed on Jan. 30, 2017.

(51) Int. Cl.
*G06F 3/01* (2006.01)
*A63B 24/00* (2006.01)
(Continued)

(52) U.S. Cl.
CPC ............ *G06F 3/011* (2013.01); *A43B 3/0005* (2013.01); *A61B 5/112* (2013.01); *A63B 22/02* (2013.01); *A63B 24/0021* (2013.01); *A63F 13/24* (2014.09); *G06F 3/0334* (2013.01); *A43B 1/0054* (2013.01); *A63B 22/0023* (2013.01); *A63B 22/0235* (2013.01); *A63B 2022/0271* (2013.01); *A63B 2024/009* (2013.01);
(Continued)

(58) Field of Classification Search
None
See application file for complete search history.

(56) References Cited

U.S. PATENT DOCUMENTS 6,152,854 A * 11/2000 Carmein .............. A63B 22/025
482/4
2007/0109259 A1* 5/2007 Liu .......................... G06F 3/011
345/156

(Continued)

*Primary Examiner* — Joseph R Haley
(74) *Attorney, Agent, or Firm* — Marsh Fischmann & Breyfogle LLP; Kent A. Lembke

(57) ABSTRACT

A modular floor with active tiles that utilize numerous friction or contact disks each with a raised segment or portion on their edges that together provide a planar contact surface for the active tile. Each disk is oriented at a fixed tilt angle to define which part of the disk's outer surfaces act as the raised portion, and each disk is oriented to position where the raised surface is located so as to define the direction that a supported object is moved over the modular floor. The drive system typically includes, for each disk assembly, a disk orienting mechanism along with a disk rotation mechanism to rotate the disk at a rotation rate about its central axis. The controller of the motion system operates the disk orienting mechanism to orient the disk so that a particular location on the disk behaves as the raised portion where an object is contacted.

20 Claims, 31 Drawing Sheets

(51) Int. Cl.
  *A63B 22/02* (2006.01)
  *A63F 13/24* (2014.01)
  *A43B 3/00* (2006.01)
  *A61B 5/11* (2006.01)
  *G06F 3/033* (2013.01)
  *A63F 13/214* (2014.01)
  *A63B 22/00* (2006.01)
  *A63B 71/06* (2006.01)
  *A43B 1/00* (2006.01)
  *A63F 13/28* (2014.01)

(52) U.S. Cl.
  CPC ........ *A63B 2024/0025* (2013.01); *A63B 2071/0638* (2013.01); *A63B 2071/0655* (2013.01); *A63B 2225/50* (2013.01); *A63F 13/214* (2014.09); *A63F 13/28* (2014.09); *A63F 2300/8082* (2013.01); *G06F 2203/012* (2013.01)

(56) References Cited

U.S. PATENT DOCUMENTS

2009/0058855 A1* 3/2009 Mishra ............... B65G 13/10
  345/427
2017/0336860 A1* 11/2017 Smoot ................ G06F 3/011

* cited by examiner

FRONT VIEW

SIDE VIEW

FLOOR SYSTEM PROVIDING OMNIDIRECTIONAL MOVEMENT OF A PERSON WALKING IN A VIRTUAL REALITY ENVIRONMENT

CROSS REFERENCE TO RELATED APPLICATIONS

This application claims priority to U.S. Provisional Pat. Appl. No. 62/452,060, filed Jan. 30, 2017, which is incorporated herein by reference in its entirety.

BACKGROUND

1. Field of the Description

The present description relates, in general, to providing mobility to people in a virtual reality (VR) environment, and, more particularly, to a system (and corresponding control method) configured to allow multiple participants in a VR environment to have the sensation of moving (e.g., walking) about the space in any direction and for unlimited distances without collisions with the other moving participants, with objects in the space, and/or with physical borders of the space.

2. Relevant Background

Virtual reality (VR), which is also known as augmented reality, immersive multimedia, and computer-simulated reality, is a computer technology that replicates a real or imagined environment and simulates a user's presence in the environment in a way that allows the user to interact with the environment. VR systems can create environments that artificially create a variety of sensory experiences such as sight, sound, and even touch (e.g., through haptic feedback devices) and smell in some cases. Most VR systems include a special VR headset with additional simulations to provide sensory information in addition to visual input such as sound and air movement.

VR environments can be quite detailed and immersive with present technologies and control techniques, but there remain a number of challenges for the designers of new VR systems. For example, designers of VR systems often aspire to provide a VR environment like science fiction models in which it is possible to have a hyper-real surrounding that seems infinite in span. To this end, it has long been desired to allow users or VR participants (e.g., people wearing VR headsets) to not have to be stationary (e.g., seated or standing in one space or one location). Instead, it is a goal to have the users walk around freely and in any direction, even over long distances, without running into the walls of the space used to provide or enclose the VR environment. Additionally, it is desirable for two or more users to be able to use the space at the same time, with each being able to follow their own path (e.g., move in any direction and different directions from the others in the VR space).

A number of approaches have been tried to allow a VR user to have the sensation of walking while in a VR environment, but none have been wholly successful in meeting the needs of VR system designers. Some VR systems have utilized a single omnidirectional treadmill, but this is limited to a single user as are similar devices such as a motorized spinning platform that can move in several directions. Another approach involves the use of large, multi-directional treadmills (e.g., with belts crossing each other) on the floor of the VR space. However, these devices are mechanically complex as they employ myriad separate moving belts under the user. This results in a very noisy environment which can hamper the VR experience and can cause safety concerns with some prototypes using a special safety harness to avoid having the user fall down or being thrown off the device. Further, to date, the VR treadmills have only allowed one user at a time in the VR environment.

In a much simpler design, the user wears slippery shoes and stands in a bowl-shaped support platform. The user continuously slips to the bottom of the bowl as they try to walk forward in any direction. This provides a relatively poor approximation of distance walking, and the system has slip and fall hazards associated with its use. Again, the system is limited to a single user, who often is strapped in to allow the device to help pull her toward the center of the bowl-shaped support platform. In other VR systems, a spherical cage similar to a large hamster ball has been used, but such VR systems require a significant amount of space to implement and, again, are limited to a single user.

SUMMARY

The inventors recognized that a motion or "walking" system may be provided for inclusion in VR systems (and in other applications) that builds upon prior efforts to move an object on a surface. These prior efforts include a system for providing preferential (or changeable or differential) friction to objects supported by a vibrating surface. The "vibrating" surface may be, for example, an upper or contact surface of a moving X-Y element that is rapidly moved, in an alternating manner, in the X direction and then in the Y direction. The system may use a variety of technologies or techniques to selectively cause the object to grab or be attracted to the contact surface.

With this system, the object moves with the rapidly moving contact surface, in the X or in the Y direction, when the friction is higher to lock the object to the surface, but the contact surface moves without the object (underneath the object) when the friction is at a lower value. By selectively switching the friction or grabbing/locking force between the higher or lower value, the object can be moved about the contact surface in a controlled manner. If multiple objects are provided on the contact surface, each of the objects may be moved in an independent and/or individually controlled manner. In this past work, a surface of a table was vibrated first in the X direction and then in the Y direction, and objects on the table were able to vary their friction with the table's upper surface instantaneously to "grab" hold of the table when it is moving in the direction that they want to go and decrease their hold on the table to let it slide under them when the table returns to a home position.

Such "inch worm" type movement is extremely effective and can independently move objects in any direction on a vibrating surface and at relatively high speeds (e.g., when high table movement frequencies are utilized in the motion system). This prior device, though, would likely have limited use or application for moving multiple participants in a VR environment. Particularly, the inventors understood that it would generally be impractical to put people on a single huge platform and move the entire platform up and down and then left and right (in X and Y directions) and individually try to control each participant's friction with this huge vibrating surface.

In another motion system taught herein for use with VR systems, it was determined that it is perfectly feasible to break such a vibrating surface into individual "active tiles" that together form the VR floor or support platform (which may be planar or substantially planar). Each active tile has a tile actuation system associated with it (e.g., provided underneath each tile) that moves the individual tile rapidly (but, typically, imperceptibly to the VR user) in the X and Y directions.

Additionally, the prior system was improved upon with this additional or second motion system by configuring the motion system in how preferential friction is obtained. In some embodiments of the motion system, the surface of each active tile can be made to instantly vibrate up and down by its tile actuation system at a high frequency (e.g., 30 to 50 kilohertz (kHz) or higher frequencies) to provide movement of the upper tile surface in the Z direction. For example, the tile actuation system may include piezo-electric transducers to instantaneously provide this Z-direction vibration to reduce the friction between a user's shoe and the upper tile surface. In other exemplary motion systems, ultrasonic transducers are provided on the upper surface of the tile or on the lower surfaces of the user's shoes to selectively reduce the friction between the user's shoes and the upper tile surface.

Control signals from a controller are sent to a tile actuation system which synchronizes and phases the instantaneous X-Y movements of the tile with the instantaneous reductions in friction to move a VR participant or user standing on or walking on the tile in a VR floor or support platform. The movement may be in any direction such as in a direction that is opposite the present direction in which the VR participant is walking to avoid a collision with a wall enclosing the VR space or with another VR participant in the VR space. The VR participant may be walking or may simply be standing on a tile (and the movement provided by the tiles may be associated with a movement in the VR environment provided at that time by operations of the VR system).

The location of the VR participant and their direction of travel are monitored/determined (such as by the VR system's location tracking assembly/components), and their location and predicted travel direction and/or path in the space are used (along with the location and travel paths of other VR participants) by the controller to control a number of adjacent or nearby active tiles to control the VR participant's location within the VR space to avoid collisions or to otherwise position each of the VR participants within the VR space. With such a motion system, a VR system can operate to provide a VR environment with media displayed (e.g., on screens on the VR space walls or by VR headsets) and can portray huge vistas and as the VR participant moves (e.g., walks) toward an object in a displayed vista they can be moved subtly backwards (opposite their present direction of movement along their presently predicted travel path) in the VR space. In this way, the VR participant has the sensation of walking significant distances in the VR environment such as toward a distant object that may appear to become closer as the walking motion causes the space to be decreased but without ever reaching the walls of the VR space.

In some embodiments, it may be desirable to utilize a modular floor in the motion system that does not rely on translational motion of the tile's contact surface combined with varying friction. Particularly, a new alternative embodiment of the modular floor may use different tile assemblies or active tiles that, instead of an inch worm manner of motion, utilize numerous friction or contact disks each with a raised segment or portion on their edges that together provide a planar contact surface for the tile assembly/active tile. Each disk is oriented at a fixed tilt angle (e.g., 10 degrees or another useful tilt angle that may be in the range of 5 to 60 degrees or another useful range) to define which part of the disk's outer surfaces/edges act as the raised segment/portion, and each disk is oriented to position where the raised surface is located so as to define the direction along X and Y axes that a supported object is moved over the modular floor (made up of a plurality of such active tiles/tile assemblies) as the numerous discs in each active tile are concurrently rotated in the same rotation direction (and with the discs being oriented similarly).

The drive system typically includes, for each disk assembly, a disk orienting mechanism along with a disk rotation mechanism to rotate the disk at a desired rotation rate about its central axis. A drive/motor may be provided for each disk assembly or for sets of such disk assemblies in the overall tile assembly. Hence, the controller of the motion system acts to define for each active tile/tile assembly an operating mode, which causes, for all the disk assemblies in the active tile/tile assembly, the disk orienting mechanism to orient the disk so that a particular location on the disk behaves as the raised portion where an object is contacted and to also define a rate of rotation of the disk about a rotation axis of the disk assembly via operation of the disk rotation mechanism (and/or drive motor).

More particularly, a floor system is described herein that is configured for providing omnidirectional movement of a supported object such as a person's shoe. The floor system includes a plurality of disk assemblies, and each of the disk assemblies includes a contact disk with an upper contact surface supported at a tilt angle relative to horizontal (that may be fixed or may be changed on the fly/during operations) so that the contact disk has a raised portion for supporting an object placed on the floor system. The floor system also includes a drive system with a disk orienting mechanism and a disk rotation mechanism for each of the disk assemblies. The floor system further includes a controller that (during each operating period of the floor system) first operates the disk orienting mechanism for each of the disk assemblies to orient the contact disk to set a location of the raised portion and second operates the disk rotation mechanism for each of the disk assemblies to rotate the contact disk about a rotation axis at a rotation rate.

In some embodiments, the tilt angle is in the range of 5 to 60 degrees (e.g., 5 to 15 degrees with 10 degrees being used in some preferred implementations). Each of the disk orienting mechanisms may include a swashplate with an angled upper surface supporting the contact disk, the swashplate is rotatable about the vertical axis to define the location of the raised portion of the contact disk. In such cases, each of the disk rotation mechanisms may include a drive shaft pivotally coupled at a first end to a lower surface of the contact disk and driven at a second end to rotate at the rotation rate. The drive shaft can extend through a center portion of the swashplate, whereby the swashplate is rotatable independent from the drive shaft. The drive system may include a first drive assembly for concurrently rotating a plurality of the swashplates to define the location of the raised portion for an array of the disk assemblies. A second drive assembly may be provided in the drive system for concurrently rotating a plurality of the drive shafts to rotate at the rotation rate in each of the disk assemblies in the array of the disk assemblies. In some cases, the floor system is modular with a plurality of active tiles, and the array of the disk assemblies is provided in one of the active tiles.

In some embodiments of the floor system, the disk rotation mechanism for each of the disk assemblies includes a motor and a drive shaft coupled to the contact disk and rotatable by the motor. Then, the disk orienting mechanism may include a motor linkage (e.g., a linkage plate or bar) pivotally coupled to a plurality of the motors that is operable (e.g., with a push-pull drive) to set an angle of the drive shafts (which are driven by the plurality of motors) to define the locations of the raised portions of the contact disks coupled to the drive shafts. In some implementations of the floor system, the disk rotation mechanism for each of the disk assemblies is adapted to rotate the contact disk only when a load greater than a predefined minimum value is applied to the raised portion of the contact disk. In other cases, the floor system further includes a magnetically transparent sheet covering and adjacent the contact disks. In such floor systems, each of the contact disks includes at least one permanent magnet element on the upper contact surface, and the support object includes one or more magnets or one or more ferrous elements in a base portion (e.g., in a sole or subsole of a shoe).

DETAILED DESCRIPTION

Figure 1A:
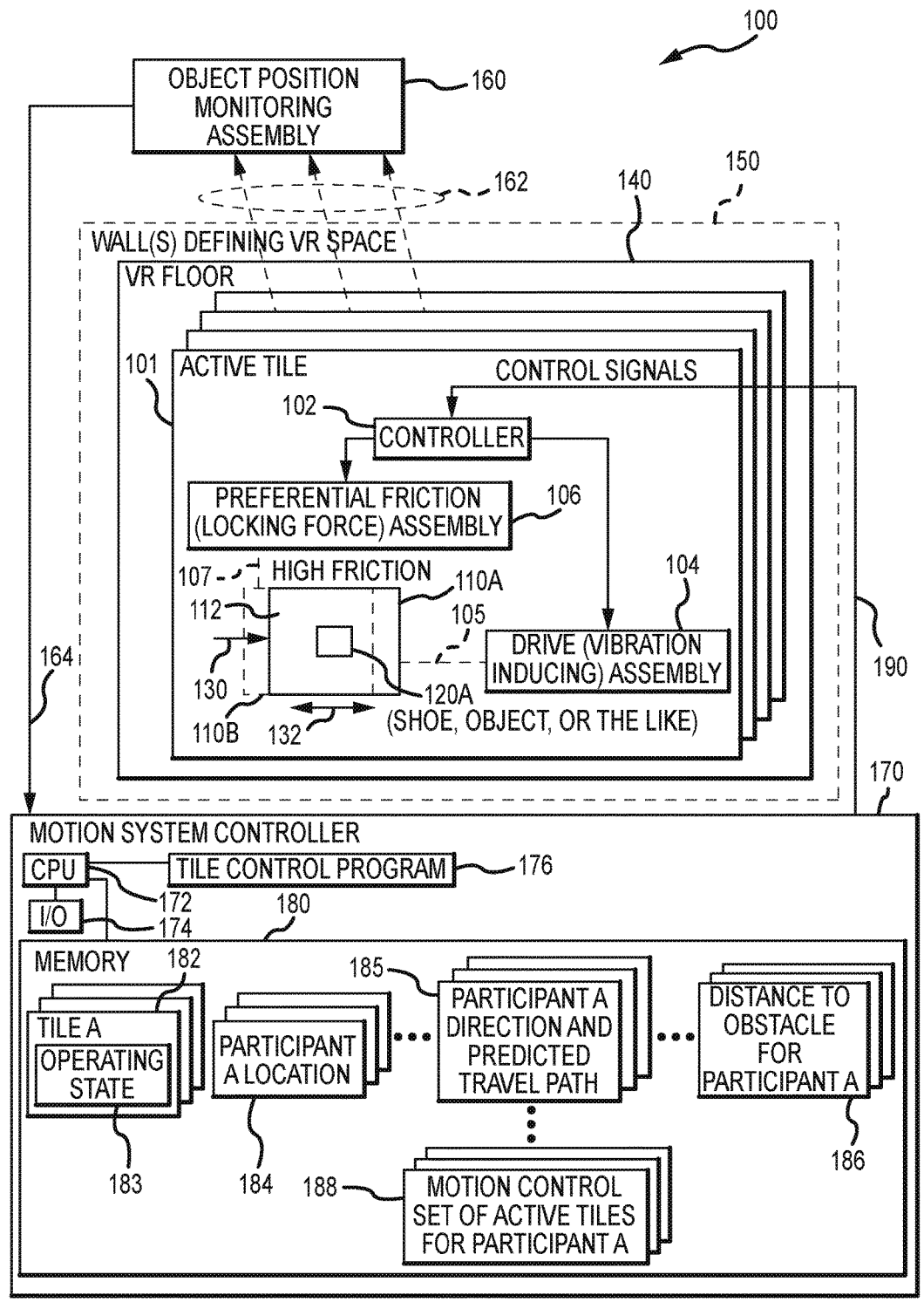
FIGS. 1A-1D illustrate functional block diagrams of an exemplary motion system (implemented as part of a VR system) using preferential friction (or a selectively applied attractive force) combined with a rapidly vibrating contact surface (a top or upper surface of modular floor or platform made up of upper or contact surfaces of a plurality of active tiles) to walk or move objects in a controlled manner.
Figure 1B:
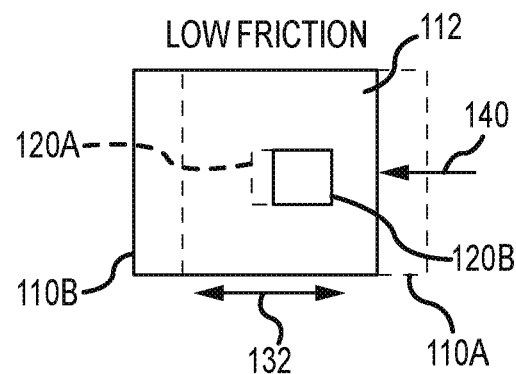

Briefly, a motion system is provided that is specially adapted to independently move multiple objects in multiple (and, often, differing) directions across its upper support surface. The motion system includes a modular floor with an upper support surface provided by a plurality of active tiles arranged side-by-side or in an adjacent design or pattern with small (e.g., 0.25 inches or less) spacing between the tile edges/sides. The tiles are "active" in that each tile can be independently operated or driven separately to move an object upon its upper surface in any direction (any direction in a horizontal plane defined by the upper surfaces of the active tiles). The object may be a virtual reality (VR) participant/user or, more specifically, a shoe or foot of the VR participant presently being supported by the active tile's upper surface, and the motion system can control (with a motion system controller) a set of the active tiles to move each object about the upper surface of the modular floor by determining a present location of the object (e.g., the VR participant), by predicting a path for the object (e.g., is the VR participant facing a particular direction and walking/moving in that direction or standing still?), by determining the presence of any objects in the predicted path, and by selecting a group or number of the active tiles to impart a motion to the object (e.g., move the VR participant in a direction opposite of their current direction of travel along the predicted path to avoid a collision (e.g., with a wall defining a VR space or with another VR participant in the VR space)).

The present description will first provide a general description of how each active tile in a motion system may operate to move an object in the context of a VR system (e.g., system 100 of FIG. 1) and then turn toward specific active tile implementations. The description also will provide a control method for use in operating a motion system with a plurality of active tiles to concurrently affect motion of multiple objects in multiple directions. The present description then turns from motion systems utilizing preferential friction and tile translational motion to motion systems that use a modular floor formed of a plurality of active tiles/tile assemblies. Each active tile/tile assembly in such a modular floor includes an array of disk assemblies. Each disk assembly includes a friction or contact disk that is set at a tilt angle (e.g., 5 to 60 degrees or the like with some prototypes successfully using a tilt angle of about 5 degrees with others planned for tilt angles of about 10 degrees (e.g., a range of 5 to 15 degrees may be preferable in some implementations)) and then oriented to define a location (or range of locations) about its edge or periphery that acts as a raised segment or portion of the disk's upper (or exposed) surface for supporting an object. Together all the raised segments/portions act as a planar support surface for the tile. The disks are then concurrently rotated about their rotation axes to cause a supported object to move in either direction (+ or −) along the X-axis or the Y-axis of the active tile or, more typically, in any direction (at any angle from the X and Y axes). Hence, the movement provided may be thought of as being omnidirectional in that it can be controlled to be "all angles" and "all directions" by proper placement of the raised segment or portion of the rotating friction/contact disks.

Each active tile may be thought of as a system adapted for selectively applying a preferential friction or attractive/locking force to objects on or contacting a contact surface or upper surface of the tile. The contact surface may be the planar surface (e.g., the upper surface) of a vibrating element. The vibrating element or active tile is caused to move first in an X-direction and then in a Y-direction (in a first direction and then in an orthogonal second direction), and the movement is very rapid and the direction is altered over time. By applying an increased friction or attractive/locking force to an object (such as a VR participant's shoe) on the contact surface, the object can be caused to move with the vibrating element or active tile in the X or Y direction. Then, by lowering the friction or attractive/locking force, the object is released or unlocked from the contact surface, and the object remains in place (generally) while the vibrating member or active plate moves relative to the object in the X or Y direction. In this manner, an object can be moved about or positioned on the contact surface of each of the active tiles in a modular floor of a motion system in a controlled manner (e.g., by controlling the application of increased friction or locking forces).

Prior to turning to the figures and particular implementations of an object positioning system (or haptic touchscreen system), it may be useful to more generally describe the concepts and functions that facilitate such an active tile system to be effectively implemented. Each active tile can be thought of as including a drive system that applies a subtle horizontal vibration to the tile's contact surface in the X and Y directions while simultaneously either locking an object to the contact surface or releasing it in a manner phased to the X and the Y vibrations.

For instance, a Z-direction vibration of the active tile (or its contact surface) may be used to lock or unlock (or disengage) a finger (or a grounded object) to or from the contact surface of the vibrating element (e.g., a touchscreen device, a display device, a game component, or the like) thus during a first stroke of a horizontal vibration when the surface is not in its high friction state or locked state, so that the entire contact surface essentially slides under the finger or other object. Then, during the return or second stroke of that vibration, the Z-direction vibration may be halted (or lowered to some preset lower value) so the object moves with the contact surface, and then the cycle may start over. Each "ratcheting" movement of the object provides only a small movement of that object with respect to the contact surface, but the X-Y drive system of each active tile in the modular floor of a motion system can operate rapidly (e.g., at 30 to 50 Hz rates or other higher frequencies). Hence, the cumulative effect can be large displacement in any direction as the attractive/locking force can be phased with any combination of horizontal impulses.

FIGS. 1A to 1D illustrate a functional block diagram of a motion system 100 with a plurality of active tiles 101 in four operating states showing movement of an object (e.g., a shoe of a VR participant) in an X-direction. The active tiles 101 of the motion system 100 are arranged to provide a single planar support surface or to provide a VR floor 140 (or support platform in a non-VR application). The VR floor 140 may be surrounded by a wall (or walls) 150 that define a space for providing a VR experience or VR environment such as when VR participants (not shown in FIG. 1A) wearing VR headsets are positioned on the contact surfaces 112 of the active tiles 101 of the VR floor 140. An object position monitoring assembly 160, such as typically provided with a VR system, is provided in the motion system 100 to collect or sense information 162 to determine a present position (and direction, in some cases) of one to many VR participants (or other objects) on the VR floor 140. This location information is transmitted as shown at 164 to a motion system controller 170.

The motion system 100 includes a motion system controller 170 to generate control signals 190 to be used by the controller 102 of the drive systems of each active tile 101 to independently operate (relative to the other tiles 101) to move the object 120A (e.g., a VR participant's shoe) in a desired direction on the VR floor 140. To this end, the motion system controller 170 includes a processor 172 that manages operations of input/output (I/O) devices 174 such as a wired/wireless transceiver for communicating as shown at 164 and 190 with the position monitoring/tracking assembly 160 and the controller 102 of each active tile 101. The I/O devices 174 may also include a mouse, a touchscreen, a touchpad, and the like for allowing an operator of the motion system 100 to provide user input such as to select and/or initiate the tile control program 176.

The tile control program 176 is software (e.g., computer executable code or instructions in computer readable storage media) that is used to process the location data 164 and, in response, to generate the control signals 190. Particularly, the controller 170 includes memory 180, and the memory 180 is operated by the CPU 172 to store a record 182 for each active tile 101 with its present operating state 183. For example, each active tile 101 may be operated independently to have its drive system vibrate its contact surface 112 in particular manner while also providing preferential friction or locking forces in a synchronized/phased manner to move an object on its surface or the active tile may be "Off" or in standby operating mode awaiting signals 190 to move an object on its contact surface 112 as needed to avoid collisions or otherwise guide the object across the VR floor 140.

To this end, memory 180 is shown to store at 184 the present location of each object in the VR space or on the upper surface of the modular floor 140. Further, memory 180 is operated to store as shown at 185 a present direction in which the object (e.g., VR participant) is facing or "traveling" and also a predicted (or desired) travel path for that object (e.g., which way is the VR participant facing and are they standing still or walking/moving in the direction they are facing, which way is an object being directed according to a defined path and where should the object be moved in the future to affect travel along the defined path, and the like). The tile control program 176 is typically configured to determine these values.

Further, the control program 176 acts to determine distances 186 for the object/participant from their current location 184 to locations of other objects (other VR participants and so on) or the VR space wall 150. Based on the information 185 and 186, the control program 176 acts to choose a set of the active tiles as shown at 188 for each object/participant to affect desired motion for the object, and the control program 176 then defines the operating state 183 for each of the active tiles 182 in this motion control set 188. Control signals 190 are then transmitted to each of these active tiles 101 to cause their controller 102 to affect such operating states/operations to move an object 120A in a desired manner (e.g., move a VR participant's shoes in a direction opposite the one they are presently attempting to travel so as to avoid a collision with a VR wall or another VR participant).

The active tile 101 is shown in FIG. 1A to include a controller 102, such as a computer or computing device with a processor preforming particular functions desired herein when running executable code or software programs provided in non-transitory computer readable medium or memory. The controller 102 may initiate and control operation of a drive (or vibration inducing) assembly 104 and/or a preferential friction (or locking force) assembly 106 and may process received control signals 190 from the motion system controller 170. The active tile 101 (or its drive system) further includes a vibrating element 110A and 110B such as a structural/rigid tile or plate or the like with an upper or contact (or touch) surface 112 upon which one or more objects 120A-120D may be placed or supported (e.g., one or more shoes of a VR participant).

FIG. 1A shows that during operation of the drive system of each active tile 101 the controller 102 may use or operate the drive assembly 104, which may be physically connected or in contact with the element 110A as shown at 105 or be proximate enough to apply forces to the element 110A, to cause the element 110A to vibrate in the X-direction. This transitional movement is shown with arrow 132 and with FIG. 1A showing the vibrating element 110A and 110B in first and second positions (first and second X-axis positions). The drive assembly 104 may take many forms to practice the system 100, and a number of useful embodiments for the assembly 104 for creating rapid movement (X and Y movements, for example) of the contact surface 112 are described below in the following examples.

The controller 102 may also operate the preferential friction (locking force) assembly 106, which may be connected (wired or wirelessly) to the element 110A or object 120A as shown at 107, to selectively generate or apply an attractive or locking force between the object 120A and the contact surface 112 (or to the vibrating element 110A). For example, the object 120A may be switched between low and high friction states with the preferential friction assembly 106. As with the drive assembly, the preferential friction assembly 106 may take a number of forms to practice the system 100 with a main goal being that the applied or generated force be adequate to "lock" (make it relatively difficult for sliding to occur) the object 120A to the contact surface 112 and then "unlock" or release (make it relatively easy for sliding to occur) the object 120A from the surface 112. The controller 102 and assemblies 104, 106, 108 are only shown in FIG. 1A (for simplicity of explanation and to avoid repetition) but should be understood to also be in use in the system 100 shown in FIGS. 1B-1D as well as the system 200 of FIGS. 2A and 2B (and other systems taught herein).

FIGS. 1A to 1D are useful for explaining operation of the drive system of each active tile 101 with its drive system being operated through two full strokes, e.g., the arrow 132 shows that the vibrating element 110A and 110B moves back and forth along a first axis (i.e., in the X-direction or along the X-axis in this example) and a "stroke" may be the combination of a movement to the right and then a movement back to the left. FIG. 1A shows the vibrating element 110A in a first horizontal position (moved to the right) and, with dashed lines, the vibrating element 110B in a second horizontal position (the position to the left or along the X-axis where the surface 112 was originally prior to movement to position 110A). This movement is repeated as the element 110A and 110B is vibrated or moved back and forth in an oscillatory manner by the drive or vibration assembly 104 as shown at 105.

With reference to FIG. 1A, the vibratory element or member is moved to the right, as shown at 110A and 110B, by a force 130 applied by the drive assembly 104. Concurrently, the preferential friction assembly 106 is operated to create high friction (or a locking force) between the object 120A, and this high friction operating mode of system 100 causes the object 120A to be essentially adhered to the contact surface 112 by high friction (which may be adjustable via assembly 106 and controller 102 to suit the object 120A and/or surface 112) with surface 112. As a result, the object 120A moves 132 with the surface 112 (as the vibratory element moves from 110B to 110A).

Once (or towards the end or second half of this first or right-moving half of the stroke) the table/element is moved to the right as shown with reference number 110A, the controller 102 may operate the preferential friction assembly 106 to create a lower amount of friction between the object 120B and the surface 112 (e.g., to release the locking or attracting force). Concurrently, surface 112 is moved, such as with substantially high acceleration, by operation of the drive assembly 104 from a first or right-most position of element 110A to a second or left-most position of element 110B (back to its standing position) via application of force 140. During this phase of operation or second half of the full stroke of system 100, the friction between the object 120B is reduced using the assembly 106, and object 120B maintains its approximate position (with respect to the Earth) due to its inertia. As a result, the object 120B has shifted a distance to the right with respect to contact surface 112 (i.e., has positive translational movement relative to the X-axis).

Figure 1C:
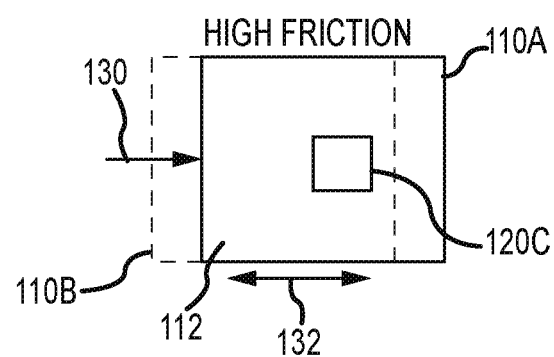

The cycle is repeated or a new stroke begins in FIG. 1C where the force 130 is applied again by the drive assembly 104 to again move the surface 112 to the right as shown with the element 110A moved from the prior or left-most position. Concurrently, the controller 102 operates the preferential friction assembly 106 to provide higher friction between the surface 112 and the object 120C (e.g., a magnitude of friction that is adequate to at least partially lock the object 120C upon the surface 112 such that the object 120C moves at least a fraction of the distance to the right with the surface 112).

Figure 1D:
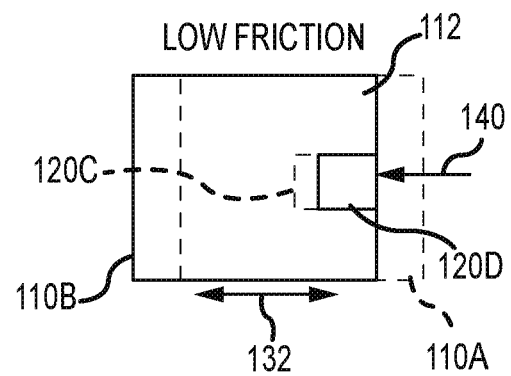

Next, as shown, in FIG. 1D, the return force 140 is again applied by the drive assembly 104 on element 110B to move it a distance to the left (from a first X-coordinate/position as shown in FIG. 1C to a second X-coordinate/position). The locking force or higher friction is removed by the operation of preferential friction assembly 106 to place the system 100 in a low friction state or operating mode. As a result, the object 120D maintains its approximate position relative to the Earth but as shown in FIG. 1D the object 120D has moved to the right relative to the oscillating surface 112. In this manner, the object 120A-120D can be walked or "inchwormed" across the surface 112 in either direction along the X-axis or moved in an X-direction (positive or negative). With the object position monitoring assembly 160, the X coordinate or location of the object 120A-120D can be determined over time, and the controllers 102 or the set of tiles (as defined at 188) may selectively operate the preferential friction assemblies 106 to move the object 120A-120D some distance to the left or right over time to move the object (e.g., a VR participant) as desired on the VR floor 140.

Figure 2A:
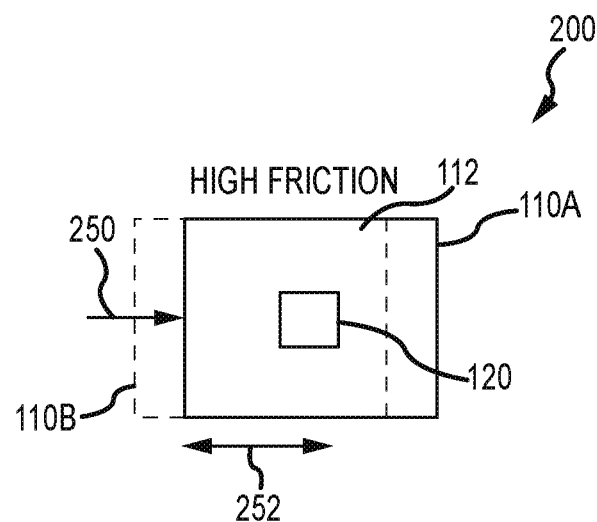
FIGS. 2A and 2B illustrate functional block diagrams of an exemplary active tile using its drive system to move an object in both X and Y directions (concurrently or sequentially)
Figure 2B:
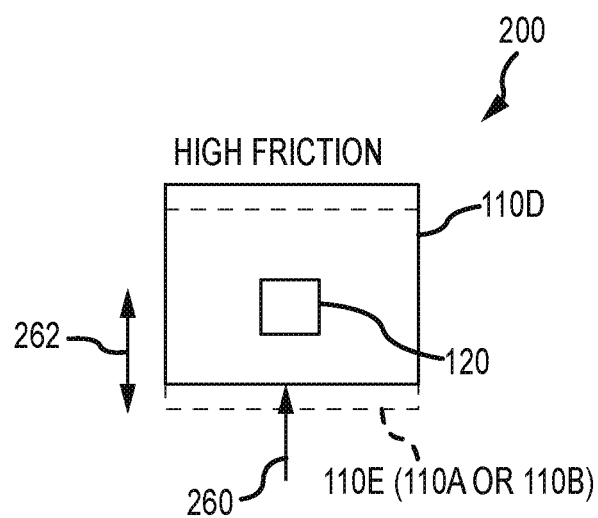

The concepts behind the system 100 may be used to move objects in arbitrary directions by creating two transverse (or non-parallel) axes of movement. For example, FIGS. 2A and 2B show an active tile 200 being operated, respectively, to move an object 120 along a first axis (e.g., the X-axis) and then along a second axis transverse to the first axis (e.g., along the Y-axis). As shown, it may be useful to drive or vibrate a table or element 110A, 110B, 110D, 110E along orthogonal axes while selectively creating a high friction and a low friction state between the object 120 and the contact or upper surface 112 of the element 110A, 110B, 110D, 110E. This allows the drive system of the active tile 200 to provide perpendicular or X-Y movement directions for the object, but it will be understood the system 200 may be configured to provide rotary and axial movement to position an object 120.

As shown in FIG. 2A, the active tile 200 is operated to vibrate or oscillate 252 the contact surface 112 in the X-direction or move it back and forth along the X-axis. As shown in FIG. 2B, the drive system of the active tile 200 is operated to vibrate or oscillate 262 in the Y-direction or move it back and forth along the Y-axis. If high friction is provided between the object 120 and the surface 112, the object 120 will move with the surface 112, e.g., from a first position of element 110B to a second position of element 110A and from a lower-most position of element 110E (e.g., with an X-axis position of 110A, 110B as shown in FIG. 2A or a position there between) to an upper-most position of element 110D. Forces 250 and 260 are applied sequentially or fully or partially concurrently to shake 252, 262 the table in the orthogonal directions.

The amount of movement and direction of the object 120 on the surface 112 is controlled by how often and when the low friction state is excited (i.e., to release the locking force and allow the object 120 to remain in a new position rather than returning with the surface 112 in the second half of each stoke of the element 110A, 110B, 110D, 110E). The amount or magnitude of movement per step can be controlled by adjusting the amplitude of movement (distance traveled from a first position of element 110A to a second position of element 110B or from a lower-most position of element 110E to an upper-most position of element 110D), the number of oscillations, and/or the amount of acceleration per move (especially during the low friction position of the movement where the surface 112 is free to slide under the object 120).

As discussed above, a wide variety of driving systems may be utilized to provide the X-Y vibratory movement of each tile/plate in a modular floor. For example, any of the drive systems or assemblies used for providing X-Y motion in U.S. patent application Ser. No. 13/874,228 ("Magnetic and Electrostatic Vibration-Driven Haptic Touchscreen"; U.S. Pat. Appl. Pub. No. 2014/0268515), which is incorporated herein in its entirety, may be utilized in the active tiles 101 such as to provide the drive assembly 104 and/or the preferential friction assembly 106 of FIG. 1.

Figure 3:
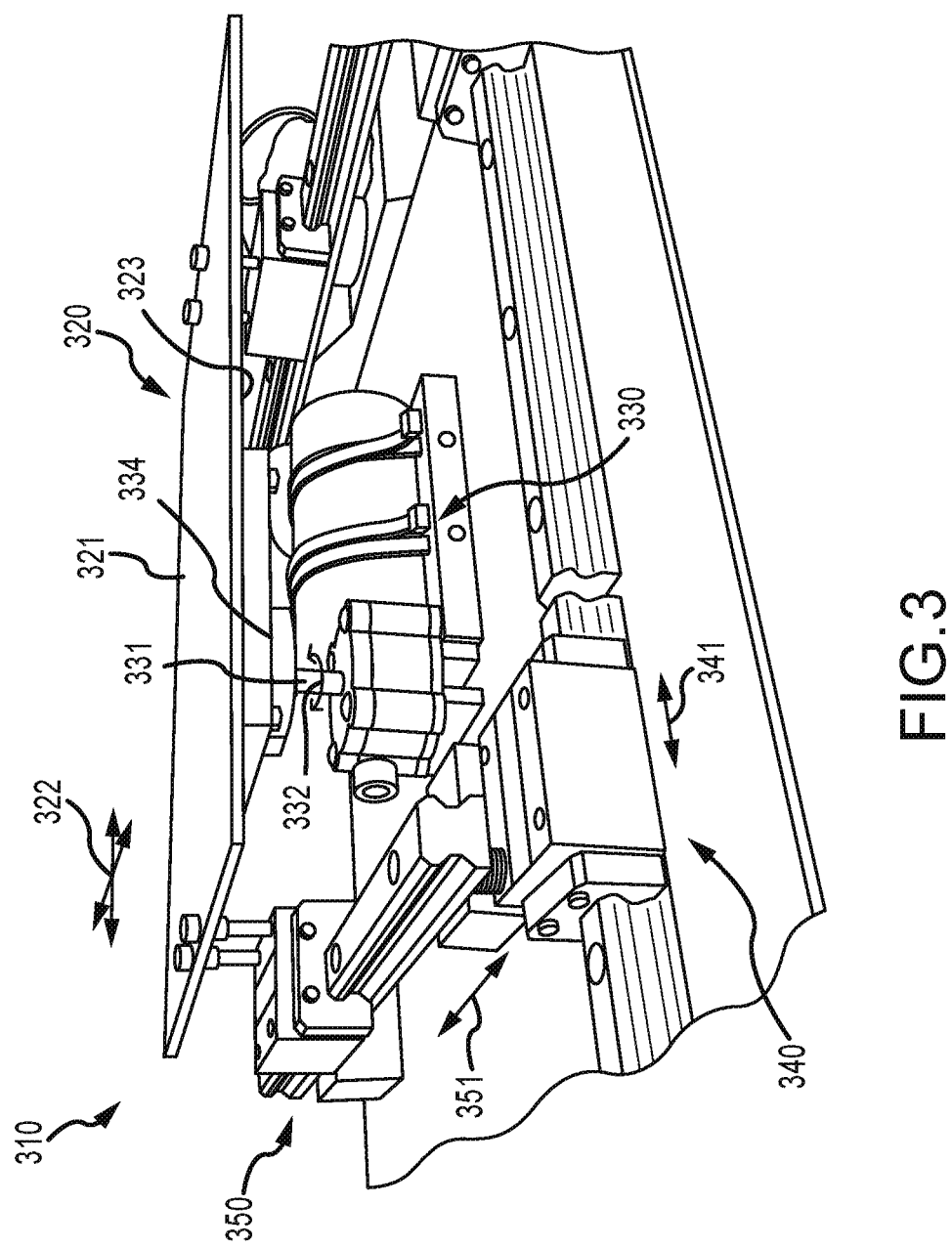
FIG. 3 illustrates an exemplary implementation of an active tile or tile assembly as may be used to fabricate, in combination with a plurality of other active tiles or tile assemblies with similar configurations, a modular floor of a motion system.

FIG. 3 illustrates an exemplary implementation of an active tile or tile assembly 310 as may be used to fabricate, in combination with a plurality of other active tiles or tile assemblies with similar configurations, a modular floor of a motion system (such as the floor 140 in the motion system 100 of FIG. 1). The active tile assembly 310 of FIG. 3 includes a support plate or tile 320 with a planar upper or contact surface 321 and a lower or attachment surface 323 opposite the upper surface 321. The tile 320 may be formed of a rigid material such as metal, a plastic, a ceramic, or the like and may take a variety of shapes and sizes. In some implementations, each tile 320 has a square upper surface 321 with 1-foot sides, but other shapes such as rectangular or triangular may be used and larger (or smaller) contact surfaces 321 may be desirable in some modular floors. During operation of the active tile 310, the tile 320 and its contact surface 321 are caused to be smoothly moved rapidly with almost no "impulsive knock" in the X and/or Y directions as shown with arrows 322. Transducers may be provided on the surface 321 or in a user's shoes, as discussed with reference to FIGS. 4-7 below, to break or overcome (interrupt) Coulomb friction between an object supported on the contact or upper surface 321 while the X and Y movements 322 are used (in a synchronized manner with reduced or increased friction) to move the object relative to the contact surface (as discussed throughout this description) in synchronization with operation of the transducers.

To provide the X and Y directional movement or vibration, an actuator or motor 330 is provided that is coupled with the lower surface 323 of the tile/plate 320. To provide the X and Y direction vibratory movement, the central motor 330 is operated to rotate 332 a vertical shaft 331. The shaft 331 extends into and is coupled with a cam assembly 334, which is affixed to the lower attachment surface 323. The vertical shaft 331 by its rotation 332 rotates a horizontal cam in the assembly 334, which rotates inside a cam-follower plate of the assembly 334. As the motor 330 rotates 332 the cam, the cam follower, which is attached to the bottom surface 323, moves the plate/tile 320 and upper contact surface 321 in a cyclical X-Y manner as shown at 322 going through the compass points (e.g., North, South, East, and West) in sequence.

Two pairs of railed or linear coupling units 340 and 350 are provided in the active tile 310 to keep the tile/plate 320 from rotating as it moves 322 back and forth and left and right. The lower linear coupling units 340 allow/facilitate a first linear movement as shown with arrows 341, and the upper linear coupling units 350 are supported upon the lower coupling units 340 to move 351 with the lower linear coupling units 340. The upper coupling units 350 are coupled to the lower surface of the tile/plate 320 to allow the first linear movement of the tile/plate (e.g., the X or Y direction movement) driven by the motor 330 and cam assembly 334.

As discussed above, the movements 322 are of a higher frequency such as 50 Hz and are relatively small in magnitude but, when synchronized with the Z-directional break in friction by an array of transducers on the upper surface 321 (see FIG. 5) or in a user's shoe (see FIG. 7), an object on the contact surface 321 can be moved effectively in any direction. Briefly, the object sticks when the plate 320 is moving slowly (e.g., attraction in the Z direction) and unsticks when the plate is moved quickly (e.g., friction broken or lessened in the Z direction). The motor 330 and cam assembly 334 combination is useful for providing such a fast movement in one direction and smooth in the other direction (fast/slow in cyclical manner). In other embodiments, though, linear actuators may be used in place of the motor and cam combination. In still other implementations, an active tile assembly may utilize solenoids/springs assemblies, gear/motor assemblies, linear motors, and the like to provide such push and pull motion to the plate/tile 320 and its contact surface 321.

Figure 4:
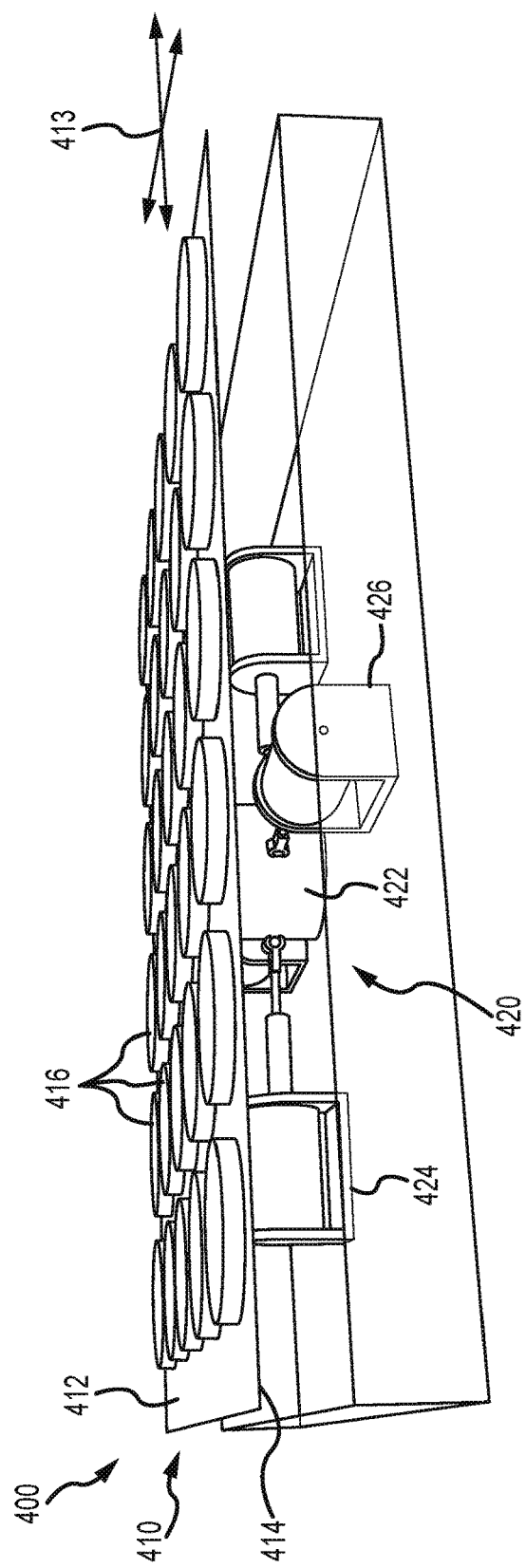
FIG. 4 illustrates a second exemplary implementation of an active tile or tile assembly as may be used to fabricate a modular floor of a motion system of the present description.

FIG. 4 illustrates a second exemplary implementation of an active tile or tile assembly 400 as may be used to fabricate a modular floor of a motion system of the present description. The active tile 400 of FIG. 4 includes a tile or plate 410 with an upper planar surface 412 and an opposite lower surface 414. The active tile 400 is adapted to provide preferential friction control via an array of ultrasonic transducers 416 that are positioned on the upper/contact surface 412 of the plate/tile 410. In use, an object such as a VR participant's shoe would contact one or more of the ultrasonic transducers 416, which may be bare as shown or which may be covered with a protective layer or sheet (not shown). When activated, the array of ultrasonic transducers 416 instantly lowers friction between any object on the tile 410 and the contact/upper surface 412.

During operations of the array of transducers 416, the plate/tile 410 is also moved (vibrated) in the X and Y directions as shown with arrows 413. This is achieved with a drive assembly 420 in the form of a central hub/support member 422 that is affixed to the lower surface 414 of the plate/tile 410. X-Y movers 424, 426 are provided that can be selectively operated by a controller (not shown in FIG. 4 but may be as shown at 102 and/or 170 in FIG. 1A) to provide rapid (e.g., 30 to 50 Hz) pushing and pulling of the hub 422 and attached plate 412. The movers 424, 426 are shown in FIG. 4 as solenoids but other actuators may be used such as air or hydraulic pistons or the like.

Figure 5:
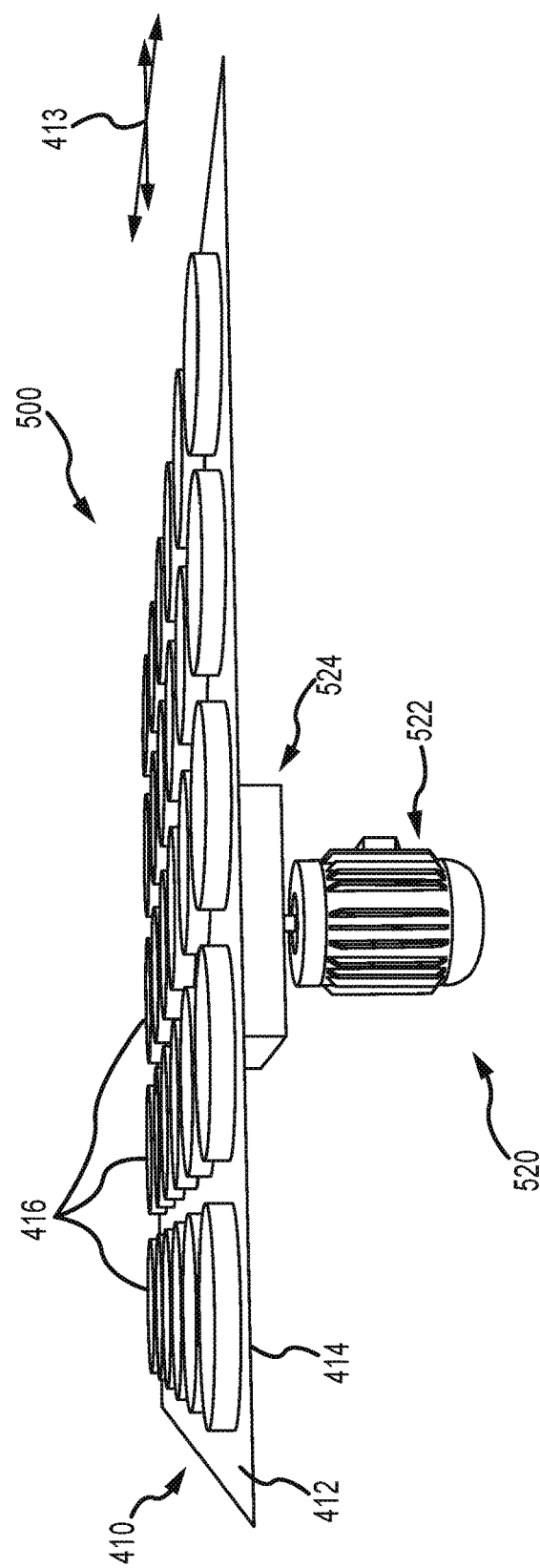
FIG. 5 illustrates a third exemplary implementation of an active tile or tile assembly 500 as may be used to fabricate a modular floor of a motion system of the present description.

FIG. 5 illustrates a third exemplary implementation of an active tile or tile assembly 500 as may be used to fabricate a modular floor of a motion system (such as system 100 of FIG. 1). In the tile assembly 500 of FIG. 5, a tile 410 with an array of ultrasonic transducers 416 is provided as in the assembly 400 to provide instantaneous friction control for any objects contacting or supported on the contact/upper surface 412. The tile 410 is also selectively moved in the X and Y directions as shown with arrows 412 as in assembly 400. In assembly 500, though, this motion 413 is provided by a drive system 520 in the form of an electric drive motor 522 with its output shaft (or drive shaft) coupled with a rotary-to-X-Y vibratory cam 524, which is coupled to the lower surface 414 of the tile or plate 410 such that the contact surface moves with this cam in response to input from drive motor 522. In this way, a single electric motor 522 can be used to provide the X-Y movement 413 rather than requiring a plurality of actuators as shown in FIGS. 3 and 4.

Figure 6:
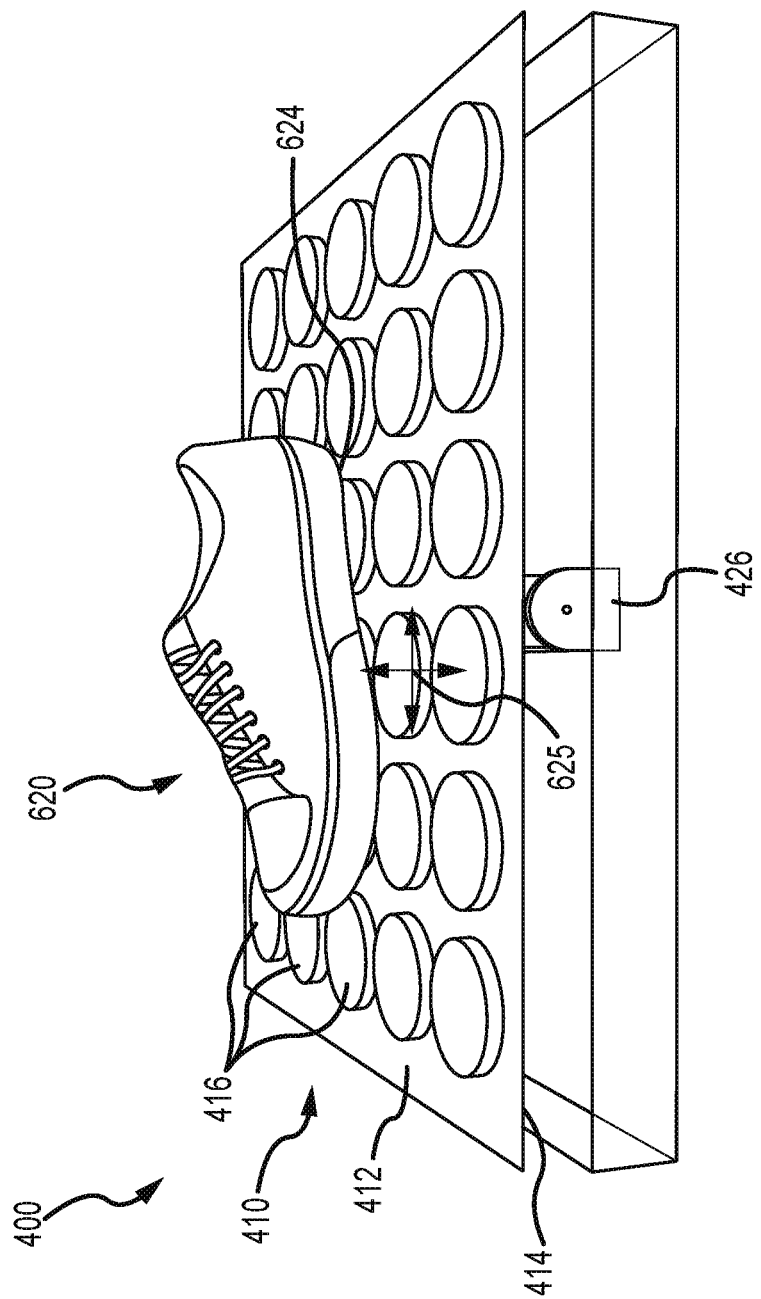
FIG. 6 illustrates the active tile of FIG. 4 during its operation or use to move footwear (or a shoe) such as would be worn by a VR participant in a VR system that includes a motion system of the present description with a modular or VR floor made up of numerous active tiles.

FIG. 6 illustrates the active tile 400 of FIG. 4 during its use, such as in combination with a plurality of other such active tiles in a modular floor, to move an object 620. As shown, the object 620 is a shoe (footwear) with a sole or lower contact surface 624 that is in contact or supported upon the upper surface 412 of the plate/tile 410 via the ultrasonic transducers 416. The sole/contact surface 624 may be relatively rigid (e.g., a semi-rigid hard plastic or rubber) and flat or planar to provide an appropriate surface for interacting with the transducers 416 to reduce friction. The operation of the transducers 416 is synchronized with operation of the plate/tile 410 and its movement 413 so as to selectively move the object 620 in any direction as shown with arrows 625. When the object 620 is a shoe or similar footwear, a person such as a VR participant may wear the object 620, and operation of the active tile 400 can be used as shown in FIG. 6 to move the VR participant in any direction via selective movement 625 of the worn/attached shoe 620 (e.g., in a direction opposite a present direction of walking/travel along a predicted travel path in a VR space or away from another object (such as a VR space wall) to avoid a collision).

Figure 7:
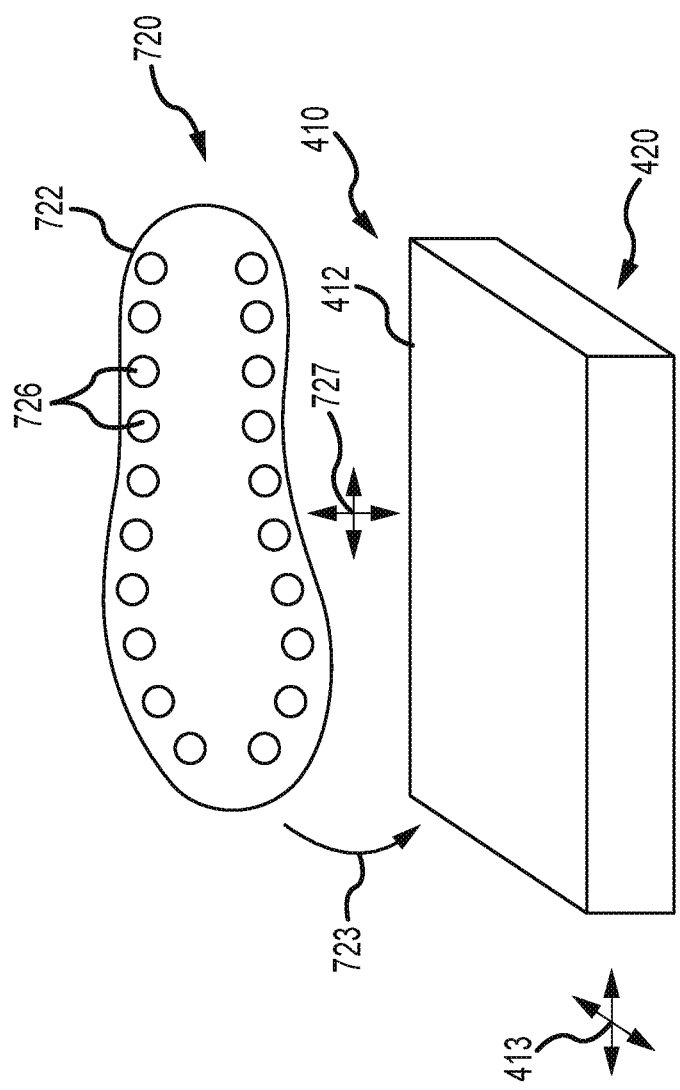
FIG. 7 illustrates a fourth implementation of an active tile and moveable object embodiment of the present description that is similar to the arrangement of FIG. 4 but with an ultrasonic transducer array provided on the bottom of the object rather than on the top/contact surface of the tile/plate.

FIG. 7 illustrates another drive system that can be used to provide motion of an object 720, which is shown as a shoe in this non-limiting example of an object configuration. As shown, the tile 410 again has a contact surface 412 and is driven with vibratory X-Y motion 413 by a drive assembly 420. In contrast to FIG. 4, though, the lower or contact surface or sole 722 of the object/shoe 720 is configured to include a plurality or array of ultrasonic transducers 726 rather than the surface 412 of the tile 410. In use, the object 720 is positioned as shown with arrow 723 in contact with the upper surface 412, and the ultrasonic transducers 726 have their operation controlled (e.g., by wired or wireless control signals from a controller of the drive system) to be synchronized with the motion 413 of the tile 412 so as to move 727 the object/shoe 720 in any desired direction (e.g., in an inch worm manner as discussed above). The power source for the transducers 726 is provided in the body of the object/shoe 720, and the transducers 726 may be bare/exposed as shown or a protective layer/sheet (not shown) may be provided to protect the transducers 726 from rubbing against the contact surface 412 of the plate/tile 410.

Figure 8:
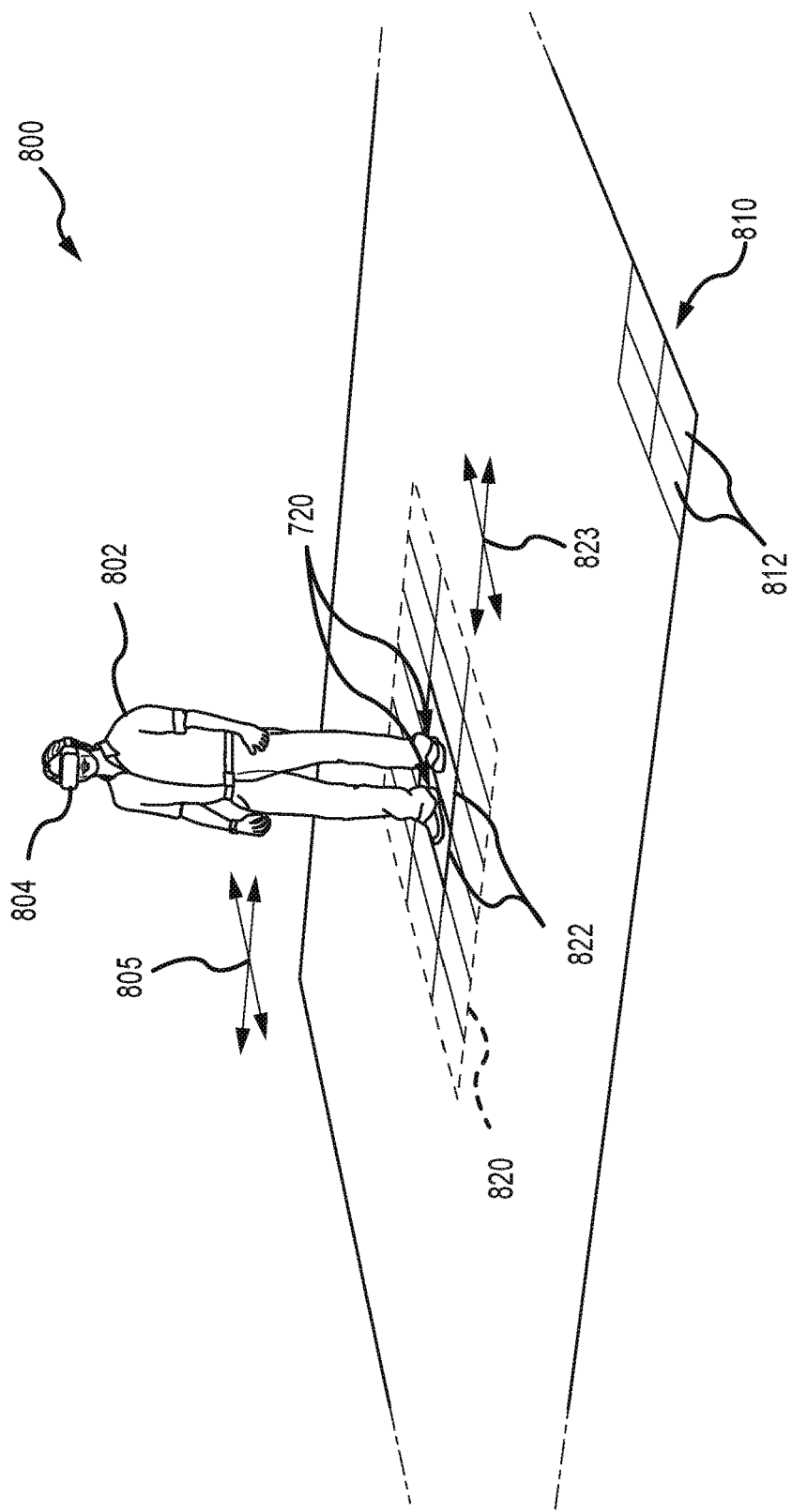
FIG. 8 illustrates a VR space with a VR or modular floor as described herein that is made up of a plurality of the active tiles and a pair of the moveable objects (e.g., a pair of shoes or footwear) shown in FIG. 7.

FIG. 8 illustrates a VR system 800 with a motion system of the present description in use to provide motion 805 to an object 802 in the form of a person wearing a VR headset 804. To this end, a modular floor 810 is provided that is formed of a plurality of active tiles 812 arranged in a side-by-side manner to provide a planar contact surface through the combination of all of their upper or contact surfaces. Each of the active tiles 812 may take the form of the active tile 400 of FIG. 410 shown in FIG. 7 (e.g., without ultrasonic transducers on the upper surface 412). The VR participant 802 is shown to be wearing a pair of the shoes 720 shown in FIG. 7 with the soles 722 and attached/embedded ultrasonic transducers 726 facing/contacting the upper surfaces of the active tiles 812 of the VR floor 810.

In the operating state shown in FIG. 8, the VR participant's shoes 720 are positioned on two side-by-side active tiles 822 (of the set of active tiles 812 of the VR floor 810), which may be concurrently and independently operated along with the ultrasonic transducers of the shoes 720 to provide selective movement 823, in any direction, of the shoes 720 and, as an additive or combined result, to the VR participant 805. In one working example, the VR participant 805 is rotated, e.g., by operating the VR floor 810 including tiles 822 and/or shoes 720 to cause the participant's left foot to move forward while moving the right foot backward with respect to the direction the participant 805 is presently facing (and vice versa to rotate in the other direction). The VR participant 802 is shown to be standing still in this example but could also be walking with the motions 823 and 805 being defined by a motion system controller to be opposite the present direction of travel along a predicted travel path (e.g., to avoid collision with one of the walls defining the VR space of system 800). In the standing still example, the motions 823 and 805 may be selected to move the VR participant 802 as desired to provide a sensation (e.g., motion that coincides with a VR experience provided concurrently by the VR headset 804) or to avoid another VR participant (not shown) or another moving object (not shown) on the VR floor 810 or in the space of the VR system 800.

Figure 9:
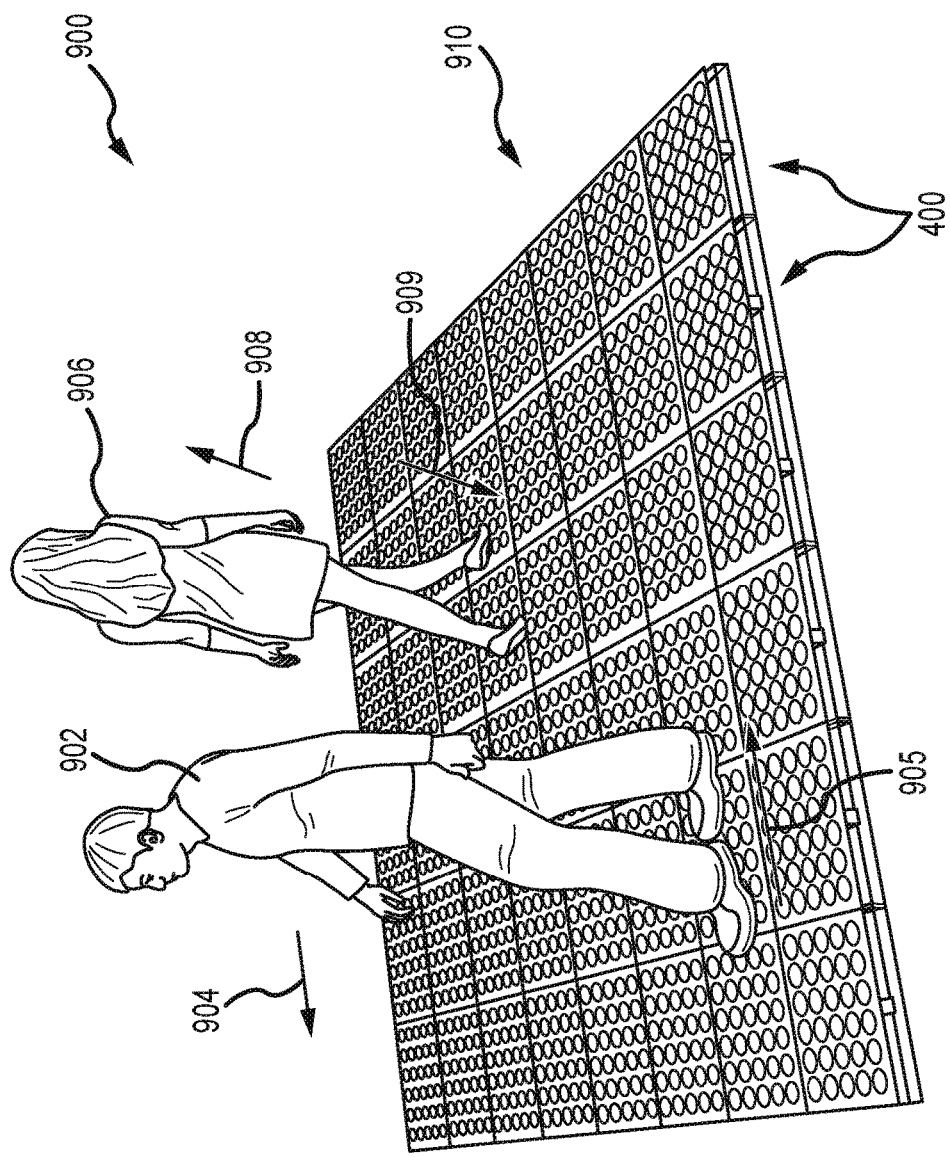
FIG. 9 illustrates another VR space with a VR or modular floor differing from that of FIG. 8 as it is formed with a plurality of the active tiles or tile assemblies as shown in FIG. 4 and also illustrating operation of the modular floor to control movement of two VR participants in the VR space who are moving independently and in different walking directions (along different travel paths)

FIG. 9 illustrates a VR system 900 with a motion system of the present description that includes a modular floor 910 formed with a plurality of active tiles 400. The active tiles 400 were shown in detail in FIG. 4 and include a drive system for providing X-Y vibratory motion and with ultrasonic transducers on their upper/contact surfaces for modifying friction between supported/contacting objects and the upper/contact surfaces of the active tiles. Again, each of the active tiles 400 may be operated independently to move any object upon their upper or contact surface.

As discussed earlier, the motion systems of the present description are particularly well-suited for use in providing motion of a plurality of objects on the modular floor 910 and its active tiles 400. As shown, for example, a VR system 900 may be used to support independent walking by two (or more) VR participants 902 and 906. The first VR participant 902 is walking in a first direction along a first travel path 904 while the second VR participant 906 is walking in a second direction along a second travel path 908 that differs from the first travel path 904.

The VR floor 910 may be (or have its active tiles 400) operated to allow the VR participants 902, 906 to walk under their own power for one to many steps. Then, when it is determined to be desired to modify this "natural" movement, a set of active tiles 400 associated with the present location and predicted travel path 904, 908 of each VR participant 902, 906 is operated concurrently and in a like manner for each participant 902, 906 to move in another direction. For example, the motion as shown with arrows 905, 909 may be opposite the current or predicted direction of travel 904, 908 so as to avoid a collision with a wall defining the space of the VR system 900, to avoid the other participant 902, 906, or achieve another desired result. The motions 905, 909 imparted to the VR participants 902, 906 are independent and concurrent even though they differ in this example. The motions 905, 909 may slow the movement 904, 908 by the VR participants 902, 906 or may even be at a rate that halts the motion (e.g., the people effectively walk in place) or that even reverses the motion (e.g., the people are moving 905, 909 at a rate that is faster than their walking pace).

Figure 10:
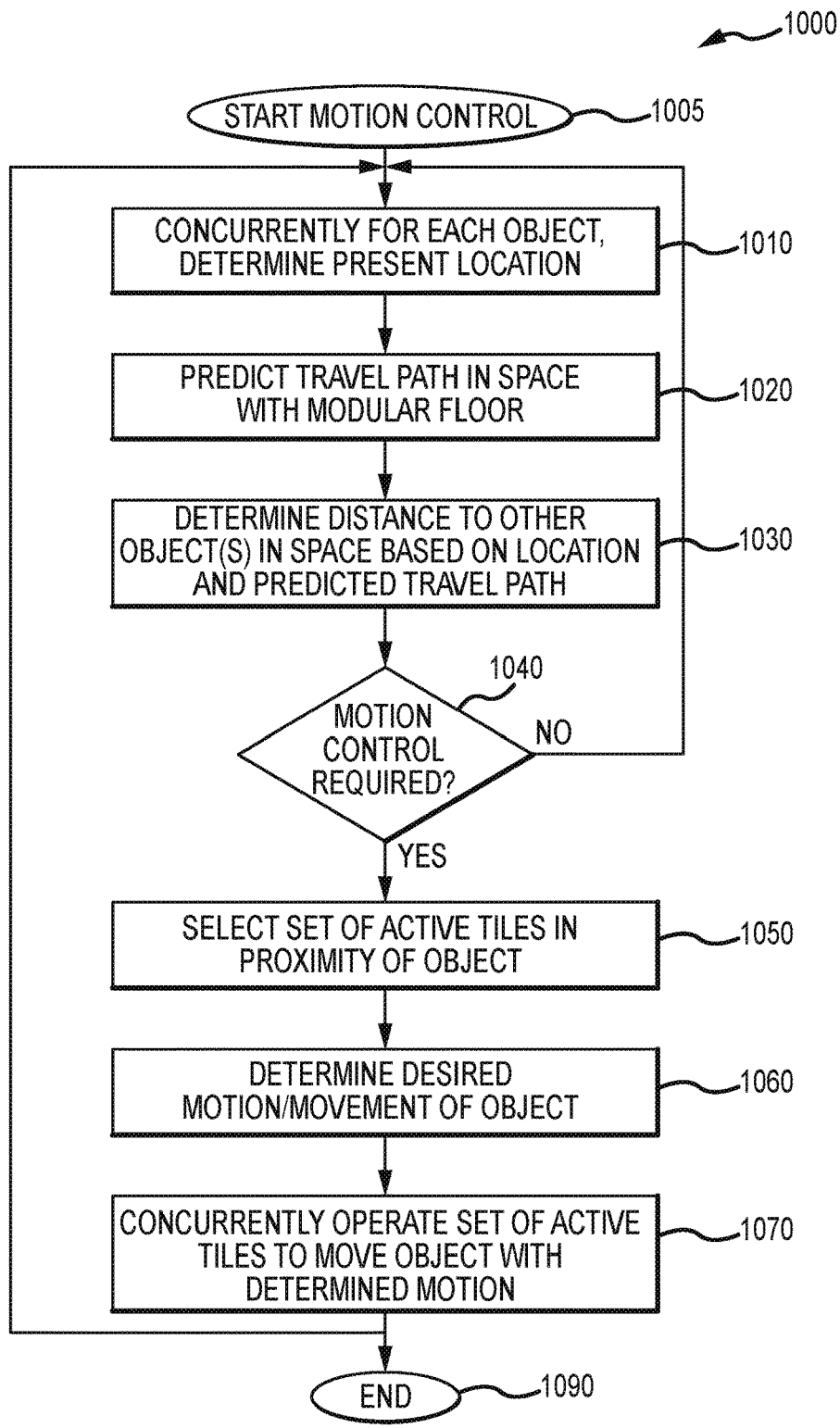
FIG. 10 provides a control algorithm or flow of operation of motion system controller as may be used during operation of a motion system of the present description (such as the system of FIG. 1)

FIG. 10 illustrates a control method 1000 for use in operating a motion system of the present description. This typically involves operating one or more of the active tiles or tile assemblies of a modular floor to move an object placed on the upper or contact surface of the modular floor through the use of X-Y directional vibrations (or rapid back and forth movements or shaking) combined with preferential friction between the object and the upper or contact surface of the modular floor (or each tile/plate making up the modular floor). The method 1000 starts at 1005 such as with installing a motion system in a space such as a space for providing a VR experience to two or more VR participants.

The method 1000 continues at 1010 with concurrently for each object in the space serviced by the motion system determining a present location of the object on the modular floor (e.g., which active tile(s) is the object supported upon). Then, at 1020, the method 1000 includes predicting a travel path in the space in an upcoming time period. This may involve determining which direction the object is facing or will be traveling and at what rate (e.g., how fast is the VR participant walking and which way are they facing?). At step 1030, the method 1000 continues with determining distances to other objects in the space based on the present location of the object and the predicted travel path. For example, a VR participant may be determined to be walking in a first direction along a linear path toward a wall enclosing the VR space, and step 1030 may determine that the VR participant is approaching the wall and is 6 feet from the wall.

The method 1000 continues at 1040 with determining whether or not motion control is desired such as to avoid collision with an object in the space or to affect a desired sensation or movement of the object through the space. If not, the method 1000 continues at 1010. If yes, the method 1000 continues at 1050 with selecting a set of active tiles in the modular floor that are to be operated to provide a desired motion or movement of the object. For example, step 1050 may involve determining the present location of the object and the predicted path, and based on this information, step 1050 may involve choosing one-to-many of the active tiles presently supporting the object and that will be supporting the object in an upcoming time period if the object continues along the present travel path (or where the object is to be moved by the imparted motion with the active tiles).

The method 1000 involves at 1060 determining the desired motion/movement of the object. For example, the information from steps 1010, 1020, and 1030 may indicate that the present movement of the object in the space has to be changed or a collision with an object will occur. In the VR example, a VR participant may be approaching another VR participant or may be approaching a wall enclosing the VR space, and step 1060 may involve determining a direction of motion that would be useful in avoiding the collision and, in some cases, a rate of such motion/movement needed. In the walking example, a VR participant may be moved at a rate and in a direction that equally opposes their walking pace and direction so that the VR participant walks in place or the rate may be greater such that the VR participant is actually moved away from the other object.

Figure 11:
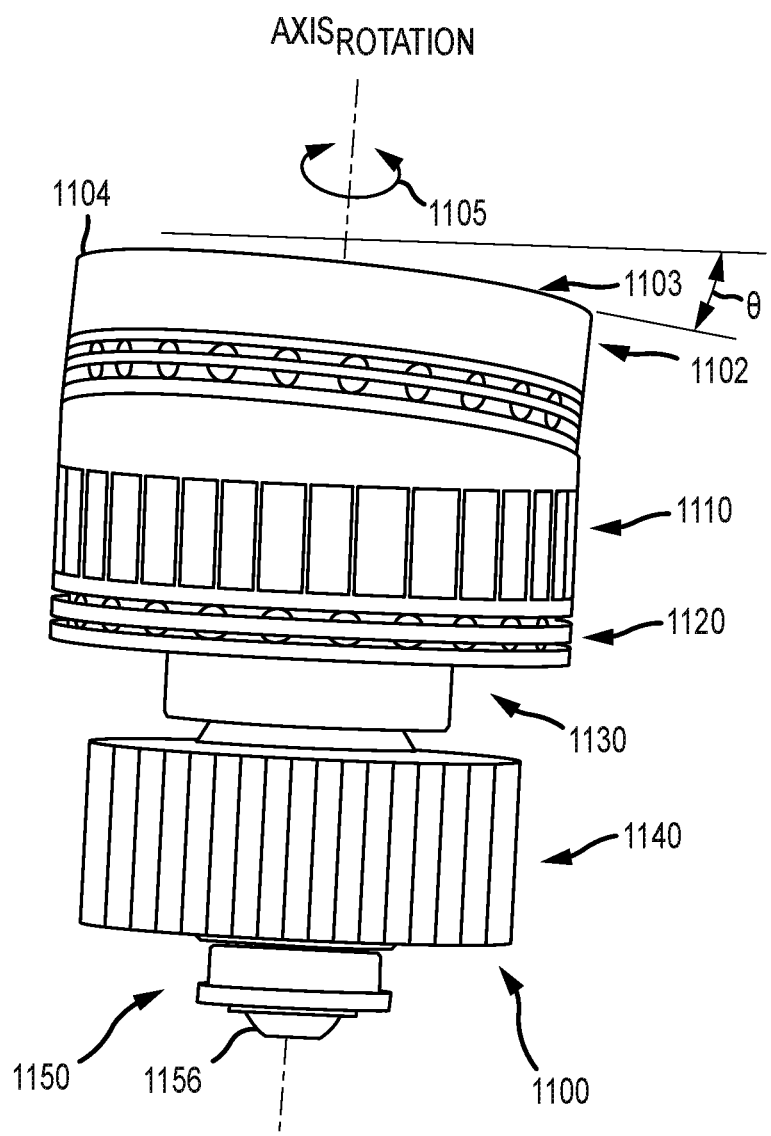
FIG. 11 illustrates a side view of a disk assembly for use in a motion system of the present description such as with a plurality of other such disk assemblies in an active tile for a modular floor.

At step 1070, the method 1000 continues with concurrently operating all of the active tiles in the set defined in step 1050 to impart the desired motion on the object (e.g., to move the VR participant via their feet/shoes in a direction and at a rate desired) such as via X-Y directional movements combined with selective changes in friction values between the object and the contact surfaces of the active tiles or using other embodiments of active tiles or tile assemblies as described below beginning with FIG. 11. The method 1000 may then continue at 1010 or end at 1090 (and the method 1000 may end at any time such as by powering down the motion system performing/implementing the motion control method 1000).

In other motion system implementations, the active tiles/tile assemblies that rely upon preferential friction and translational motion may be replaced with differently designed embodiments of active tiles (or tile assemblies), while the other components of the motion system may be reused (or modified as needed to provide useful control signals to the other tile assemblies). For example, a modular floor of a motion system may be formed with a plurality of active tiles (or disk assemblies). Each of these active tiles may be considered a mechanism/system including an array of disk assemblies, and each disk assembly includes a friction or contact disk with an upper or upward facing side. The friction or contact disks (or disk-shaped elements that may be flat, domed, conical, truncated conical, or the like in shape) are each tilted or supported at a tilt angle (e.g., an angle of 2 to 60 degrees or more with a tilt angle between 5 and 15 degrees being useful in many applications with an angle of about 5 degrees used in one prototype) to present a raised portion or segment, and the combination of the raised portions or segments of all the friction or contact disks of the active tile provides a planar support surface upon which an object such as a VR participant's shoe may be positioned and supported. The tilting of the wheel/disk (instead of having its rotation axis parallel or orthogonal to the contact surface) is desirable to increase the size of the raised segment or portion (maximize or at least increase contact area between a supported object and the rotating disk), and there is likely a sweet spot or range for the tilt angle to achieve a desirably large raised segment (contact surface) for each disk.

During operation, each of the contact or friction disks, independently or as a group (or subset), has its orientation relative to the rotation axis modified so as to define the location of the raised segment or portion (e.g., relative to the rotation axis) and where a supported object will contact the disk. Also, during operations, the disks of each active tile (independently or as a group (or subset)) are rotated about their rotation axes such that the raised segment or portion contacting the supported object is moving about the rotation axis (e.g., in a CW or CCW direction) so as to cause the supported object to move via being driven by the combination of the raised segments/portions. The orienting of the disk, e.g., in one of four locations when moving along the X and Y axes or one-to-many when moving at any of a desired angle from or between the X and Y axes, determines which direction the supported object is moved such as in either direction along the X-axis (+ or −X) or in either direction along the Y-axis (+ or −Y) or, in many operations/controls, in any direction at any angle from the X and Y axes. Hence, the movement provided may be thought of as being omnidirectional in that it can be controlled to be "all angles" and "all directions" by proper placement of the raised segment or portion of the rotating friction/contact disks relative to the rotation axis.

The speed of movement of the supported object can be controlled by varying the rotational velocity of the disks, and the direction of movement is controlled by direction of tilt (or orienting the disk relative to the rotation axis). Thus, by varying both rotation speed and tilt direction (or disk orientation), omnidirectional movement can be imparted on any object (such as a human's shoe) resting on the support surface of the active tile in the modular floor. The rotation speed (or rotational velocity) of the disks can be held constant in some embodiments or it may be varied by the system controller.

The power or drive for rotating the disks of an active tile can be provided by a small local motor for each disk (or in each disk assembly) while other embodiments may utilize a drive that uses a ganged mechanism (e.g., a set of gears, toothed belts, and the like) to drive the disk rotation mechanisms of two-to-many of the disk assemblies (e.g., provide drive from a larger, common source rather than independent motors for each disk). The orienting of the tilt or setting the direction of the tilt can be accomplished by a mechanism (i.e., a disk orienting mechanism) that sets the direction of tilt of all disks in an active tile and, thus, only requires a single tilting "motor," but other embodiments may be configured to enable single disks or groups/sets of disks to have their tilt direction or orientation be set independently.

Modular floors with such active tiles provide a user experience that is smooth, and it allows a VR participant to walk in a comfortable and natural manner. The active tiles use continuously (in some embodiments) rotating elements (e.g., friction/contact disks), which lowers friction, vibration, and power requirements compared with preferential friction embodiments. The active tile's parts are easily manufactured, and, due to the array nature of the design, each of the parts is similar to like parts in other disk assemblies such that the active tiles are amenable to mass production/replication. The floor can be constructed in either a modular manner (e.g., as individual floor tiles for later assembly with other tiles to form a modular floor) or can be constructed as a single larger installation (e.g., a floor made up of a plurality of disk assemblies driven/controlled independently or in sets of two or more disk assemblies). In some embodiments, the motion system with these disk assemblies is controlled so as to allow varying speed and direction of motion of sub-portions of the floor so as to allow faster or slower movement of an object or person on portions of the floor's surface (or through local differential movement or speeds of parts of the moved object such as to rotate the object). Because these active tiles always maintain local static friction with a user's shoes, there is no issue with the floor (support surface) feeling (or being) "slippery."

Figure 12:
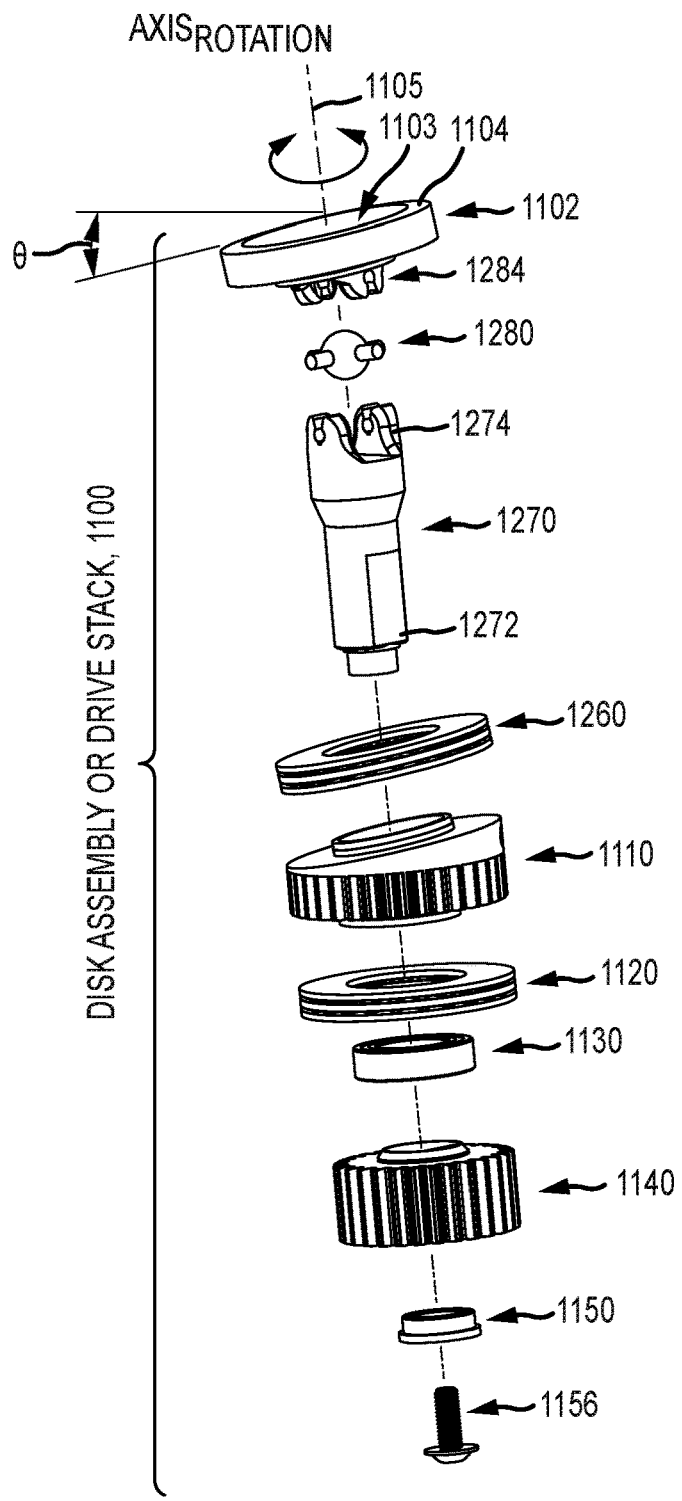
FIG. 12 illustrates the disk assembly of FIG. 11 with an exploded view showing details of each of its components.

FIG. 11 illustrates a side view of a disk assembly 1100 for use in a motion system of the present description such as with a plurality of other such disk assemblies in an active tile for a modular floor or in an array in a non-modular configuration. FIG. 12 illustrates the disk assembly of FIG. 11 with an exploded view showing details of each of its components. In FIG. 11, the disk assembly 1100 can be seen to include a contact disk 1102 on a first or outer (exposed) end with an upper or contact surface 1103 that would be used in a modular floor with a plurality of other contact surfaces of arrays of friction disks to support and move an object. The contact disk 1102 is positioned and/or supported in the assembly 1100 so as to place the upper/contact surface 1103 at a tilt angle, θ, (e.g., an angle of 5 to 60 degrees with about 8 to 15 degrees being useful in some cases and 10 degrees (i.e., 9.5 to 10.5 degrees) being useful in one prototyped implementation) such that a segment or portion 1104 is raised relative to the rest of the upper/contact surface 1103 such that this raised segment/portion 1104 (along with similar segments/portions of other contact disks in an active tile and floor) contact and support any object placed on the assembly 1100. During use, the contact disk 110 is rotated about a rotation axis, $Axis_{Rotation}$, as is shown by arrows 1105, and it can be seen that this axis, $Axis_{Rotation}$, is not orthogonal to the contact/upper surface 1103 (e.g., is at an angle of 90 degrees plus the tilt angle, θ) such that the raised segment 1104 continues to be at a predefined location during an operating period to move the supported object in a desired direction.

In the assembly 1100, a swashplate 1110 is provided with an angled upper surface is provided to support the contact disk 1102 at tilt angle, θ (constant or changed during operations). The swashplate 1110 may be drivable (e.g., be gear driven via outer teeth as shown in FIG. 11, be belt driven, or the like) to selectively change where the raised portion/segment 1104 is located relative to the rotation axis, $Axis_{Rotation}$, so as to control which direction a supported object is moved, but the swashplate 1110 may remain stationary or fixed in place relative to the axis, $Axis_{Rotation}$, during the rotation 1105 of the disk 1102. In FIG. 11, the assembly 1100 is further shown to include a lower (or intermediate) thrust bearing 1120, a radial bearing 1130, a rotation gear 1140 for rotating 1105 the friction disk 1102 about the friction disk 1102 about the rotation axis, $Axis_{Rotation}$, a bottom bearing 1150, and a fastener 1156 for securing the disk assembly or drive stack 1100 components together as an operable unit.

As discussed above, each disk assembly 1100 may include a friction or contact disk 1102 that is supported at a disk or tilt angle, θ, by a tilted swashplate 1110 and then selectively rotated 1105 about its rotation axis, $Axis_{Rotation}$, while the swashplate 1110 remains stationary, to move any object supported upon its raised edge or portion 1104 of its upper or contact surface 1103. Rotation 1105 is provided through a disk rotation mechanism (which includes at least the rotation gear 1140 seen in FIG. 11) in the disk assembly 1100 that works in combination with a drive system (not shown in FIG. 11) (e.g., one or more motors driving belts, screw drives, gears, or the like to impart motion on one or more components of the disk rotation mechanism such as upon the outer gear teeth on the rotation gear 1140). Each disk assembly 1100 is adapted to allow the disk 1102 to be oriented (e.g., rotated relative to the rotation axis, $Axis_{Rotation}$) in the assembly 1100 (such as by rotation of the swashplate 1110 about the vertical axis) to set the disk angle direction or to orient the disk (relative to the rotation axis, $Axis_{Rotation}$, and such orienting may be defined in degrees of rotation about or relative to this axis, $Axis_{Rotation}$, or the vertical axis) to set the location of the raised edge/segment 1104 relative to the vertical axis to define which direction a supported object is moved.

With reference now to FIG. 12, the disk assembly or drive stack 1100 is shown with an exploded view to include the contact disk 1102 at its upper end, and the contact disk 1102 includes an upper side/surface 1103 that is facing upwards/outwards. The upper side/surface 1103 is circular in shape in the illustrated embodiment, with an outer ring-shaped contact surface or lip that would engage surfaces of a supported object. The disk 1102 is shown to be positioned or supported in the assembly 1100 at a disk or tilt angle, θ, (e.g., an angle in the range of 5 to 60 degrees or the like as measured between a horizontal plane and the upper side/surface 1103 of the disk 1102). This causes a raised edge or portion 1104 of the ring-shaped contact surface to be used to contact and move an object (not shown) supported upon the contact disk, and this raised edge/segment 1104 may be a fraction of the ring-shaped contact surface on upper surface 1103 such as in the range of 1/10 to 2/5 of the available surface depending on the magnitude of the tilt angle, θ.

Hence, the orientation of the contacting portion or raised edge 1104 of the disk 1102 (as it rotates so the specific part of the outer ring-shaped contact surface contacting the object changes during each rotation 1105 of the contact disk 1102 about its rotation axis, $Axis_{Rotation}$) relative to the rotation axis, $Axis_{Rotation}$, defines the direction a supported object is moved by the disk assembly 1100. For example, the tilt direction or disk orientation may be set such that the raised portion 1104 is at the "top" of the contact disk 1102 (or into the page containing FIG. 12 or at 270 degrees) and the rotation direction may be clockwise (CW) about the axis, $Axis_{Rotation}$, and this would cause a supported object to be moved in a positive X direction or to the right when looking at the page containing FIG. 12. If the disk 1102 is oriented with the raised portion 1104 to the right side of the rotation axis, $Axis_{Rotation}$ (or at 0 degrees) and the disk 1102 is again rotated CW, the supported object is moved in a negative Y direction or downward when looking at the page containing FIG. 12. If the disk 1102 is oriented with the raised portion 1104 to the "bottom" of the disk 1102 (or at 90 degrees relative to the axis, $Axis_{Rotation}$) and the disk 1102 is rotated CW, the supported object is moved in a negative X direction. Further, if the disk 1102 is oriented with the raised portion 1104 to the left side of the rotation axis, $Axis_{Rotation}$ (or at 180 degrees) and the disk 1102 is rotated CW, the supported object is moved in a positive Y direction or upward when looking at the page containing FIG. 12. During any particular operation period used to move an object in a particular direction, the components of the disk assembly 1100 supporting the friction disk are configured to allow the contact disk 1102 to be oriented in any of at least these four orientations or disk directions (or intermediate positions between these four orientations) relative to the rotation axis, $Axis_{Rotation}$, and to concurrently allow the disk 1102 to be rotated 1105 at a desired rate or speed about the rotation axis, $Axis_{Rotation}$, while remaining at the tilt angle, θ, at the particular disk face orientation/direction.

To this end, the disk assembly or drive stack 1100 is shown in FIG. 12 to include a U-joint drive 1280 pivotally supported on an end 1274 of a keyed drive shaft 1270, and the U-joint drive 1280 is pivotally coupled to a bottom or lower surface 1284 of the contact disk 1102. The use of the U-joint drive 1280 allows the contact disk 1102 to be rotated 1105 while its high-point or raised portion 1104 is turned (or re-directed) via swashplate 1110 to change the orientation of the tilt or disk angle or to set the disk direction (e.g., to change an angular location of a center of the raised portion 1104 relative to the rotation axis, $Axis_{Rotation}$). The drive stack 1100 also includes a rotation gear 1140 that supports and/or mates with the drive shaft 1270 via the keyed end 1272, and the rotation gear 1140 may be gear driven (e.g., via external teeth coupled to a gear of a drive mechanism (not shown in FIG. 12)) to rotate about the rotation axis, $Axis_{Rotation}$. Rotation of the rotation gear 1140 causes the coupled drive shaft 1270 to rotate, which, in turn, causes the contact disk 1102 to rotate 1105.

To allow the contact disk to be supported at a tilt or disk angle, θ, that can have varying or controllable orientations or disk directions relative to the rotation axis, $Axis_{Rotation}$, to set the direction in which the supported object is moved, the disk stack 1100 includes a component 1110 with an angled upper surface (e.g., a swashplate or swashplate element) that can remain stationary while the shaft 1270 rotates to drive disk 1102. The swashplate element 1110 has a toothed outer surface (i.e., the swashplate element 1110 is geared) that allows it to be gear driven (e.g., rotated about the vertical axis) by a drive in a disk orienting mechanism/assembly (not shown in FIG. 12) to set the direction of the contact disk 1102 or to set the orientation or location of the raised portion 1104 of the disk 1102. A thrust bearing 1260 may be inserted between the angled upper surface of the swashplate element 1110 and the lower/bottom surface with pivotal mount 1284 of the contact disk 1102 allowing the load on the disk 1102 to be transferred downward into the stack 1100 but also allowing lower friction rotation 1105 of the disk 1102 upon the swashplate 1110. Likewise, a thrust bearing 1120 may be inserted between the swashplate element 1110 and the rotation gear 1140 for transferring overall downward load from the swashplate element 1110 onto rotation gear 1140.

The drive stack 1100 may further include a radial bearing 1130 riding on an upper surface of the rotation gear 1140 between this lower thrust bearing 1120 and the drive shaft 1270 to allow the drive shaft 1270 to rotate more freely within the stack or disk assembly 1100. The assembly 1100 further includes a bottom bearing 1150 opposite the radial bearing 1130 that acts to center the drive shaft 1270 within the assembly 1100 and to secure the assembly 1100 within a mounting plate (not shown). A fastener (e.g., a screw) 1156 may be included at the bottom of the drive shaft 1270 to secure or interconnect the assembly components.

Arrays or pluralities of the disk assemblies 1100 can be combined into tiles that can be combined to provide a modular floor of the present description or can be used in combination to provide a large floor or platform to move supported objects. Each drive assembly 1100 may be driven independently; however, it is useful in many situations to concurrently drive an array or subset of the disk assemblies 1100 used to make up a support floor/platform such as by orienting and driving/rotating each friction disk in an active tile similarly (e.g., drive each drive assembly 1100 in a floor tile concurrently and similarly to move an object on that tile in a particular direction and at a particular speed).

Figure 13:
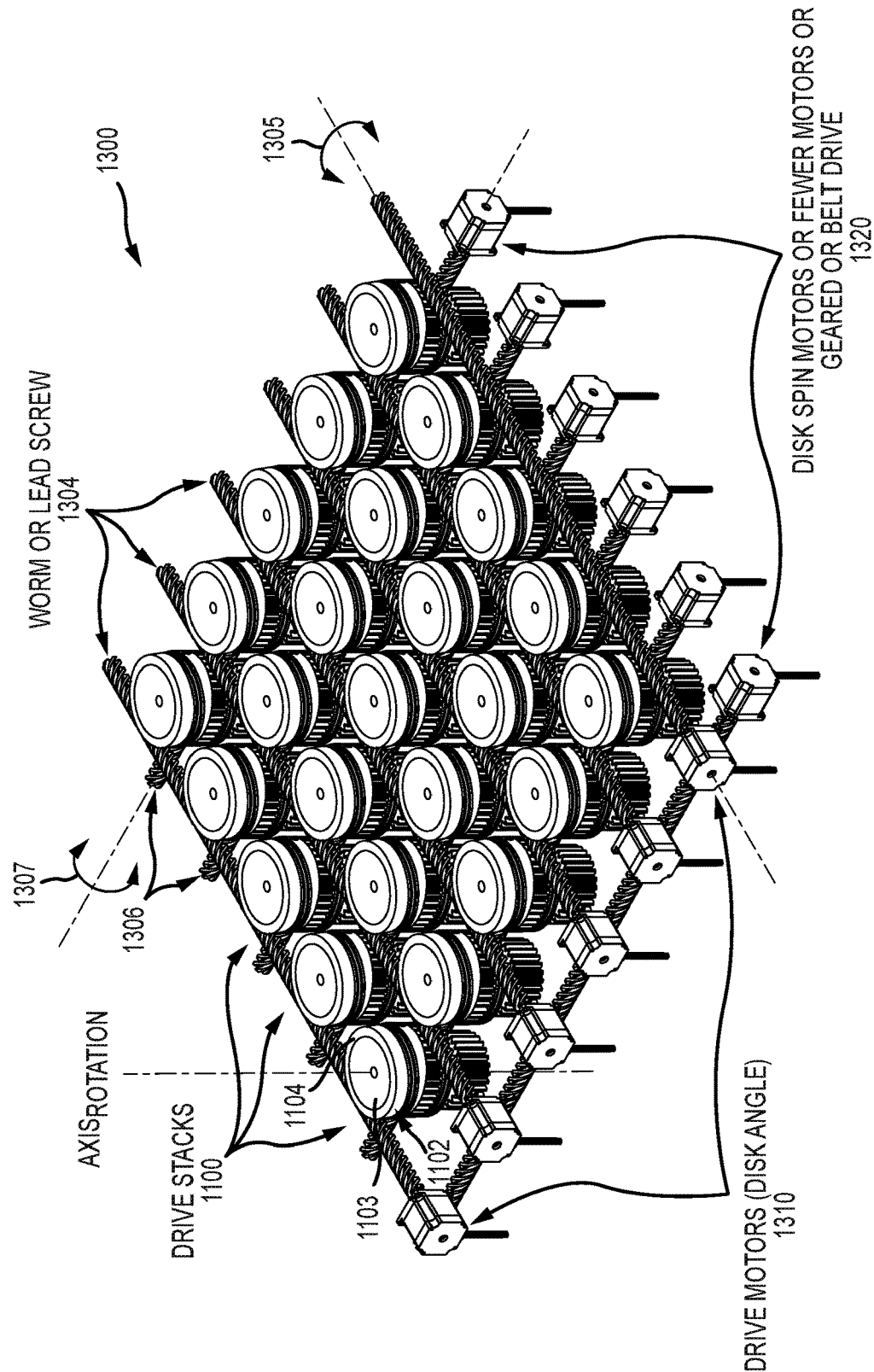
FIG. 13 is a top perspective view of a portion of a floor for a motion system (e.g., an image of an active tile or tile assembly for use in a modular floor)

With this in mind, FIG. 13 illustrates one embodiment of an active tile or tile assembly 1300 that includes an array or plurality of the drive stacks or disk assemblies 1100 arranged in a rectangular pattern with parallel rotation axes (e.g., in parallel rows and columns of disk assemblies 1100 as shown) with the upper surface 1103 of their friction disks 1102 facing a single direction (e.g., "up" or "outward" when assembled into a modular floor with a plurality of active tiles 1300). The group or array of disk assemblies 1100 are shown to be driven together as a set or concurrently to rotate at the same rate and in the same direction about their rotation axes, $Axis_{Rotation}$. Further, each friction disk 1102 is also oriented to have the same disk direction or to have their disk/tilt angles oriented in the same way. In this manner, an object supported (on the plurality of raised portions 1104) by any subset of the disk assemblies 1100 (or their contact disks 1102) would be moved in the same direction and at the same rate by operation of the disk assemblies 1100 in the active tile 1300. As shown, the raised edges or portions 1104 are generally on the right hand side of each assembly 1100 in the tile 1300 such that CW rotation of the disks 1102 would cause the supported object (not shown but understood from earlier figures/discussion) to be moved toward the lower right portion of the tile 1300.

As will be understood, the active tile 1300 may be combined with other active tiles to provide a worm or lead screw-driven floor (such as to implement VR floor 140 in system 100 of FIG. 1). In this regard, worm or lead screws 1304, 1306 are positioned to contact each of the drive stacks upon the geared/toothed outer surfaces of both the swashplate elements and the rotation gears, respectively, of each of the disk assemblies 1100. A controller of the motion system including the active tile 1300 is configured to selectively operates drive motors 1310 to cause the worm or lead screws abutting the swashplate elements to rotate 1305 as needed/desired to set the disk directions (or to orient the disk angles by rotating the swashplates with their tilted/angles support surfaces about the rotation axis, $Axis_{Rotation}$) to position the raised edges 1104 of the disks 1102 of the disk assemblies 1100 concurrently in a desired location to set the direction of travel of a supported object. Stated differently, rotation of the set of worm or lead screws 1304 by the drive motors 1310 causes the swashplate elements' upper angled surfaces to rotate about the rotation axes, which, in turn, causes the supported contact disks 1102 to likewise have its upper contact surfaces 1103 (and raised edge/portions 1104) rotated to a new location relative to each axis of rotation, $Axis_{Rotation}$, of each disk assembly 1100.

Concurrently or at a different time, disk spin motors 1320 (or fewer motors may be used that are geared or ganged together or belts may be used) are operated by an active tile controller (or system controller) to rotate 1307 a set of worm or lead screws 1306 that abut the rotation gears of the disk assemblies 1100. This causes/drives the rotation gears to each rotate about the rotation axis, $Axis_{Rotation}$, of each assembly 1100, which causes a corresponding drive shaft and interconnected contact disk 1102 to rotate in each of the disk assemblies 1100. The direction of rotation for the disks 1102 is set by the direction of rotation 1307 of the worm or lead screws 1306 by the motors 1320 (or other drives). Similarly, the rate of rotation of the disks 1102 in the stacks 1100 is set by the rate of rotation 1307 of the worm or lead screws 1306 by the motors (or other drives) 1320.

Figure 14:
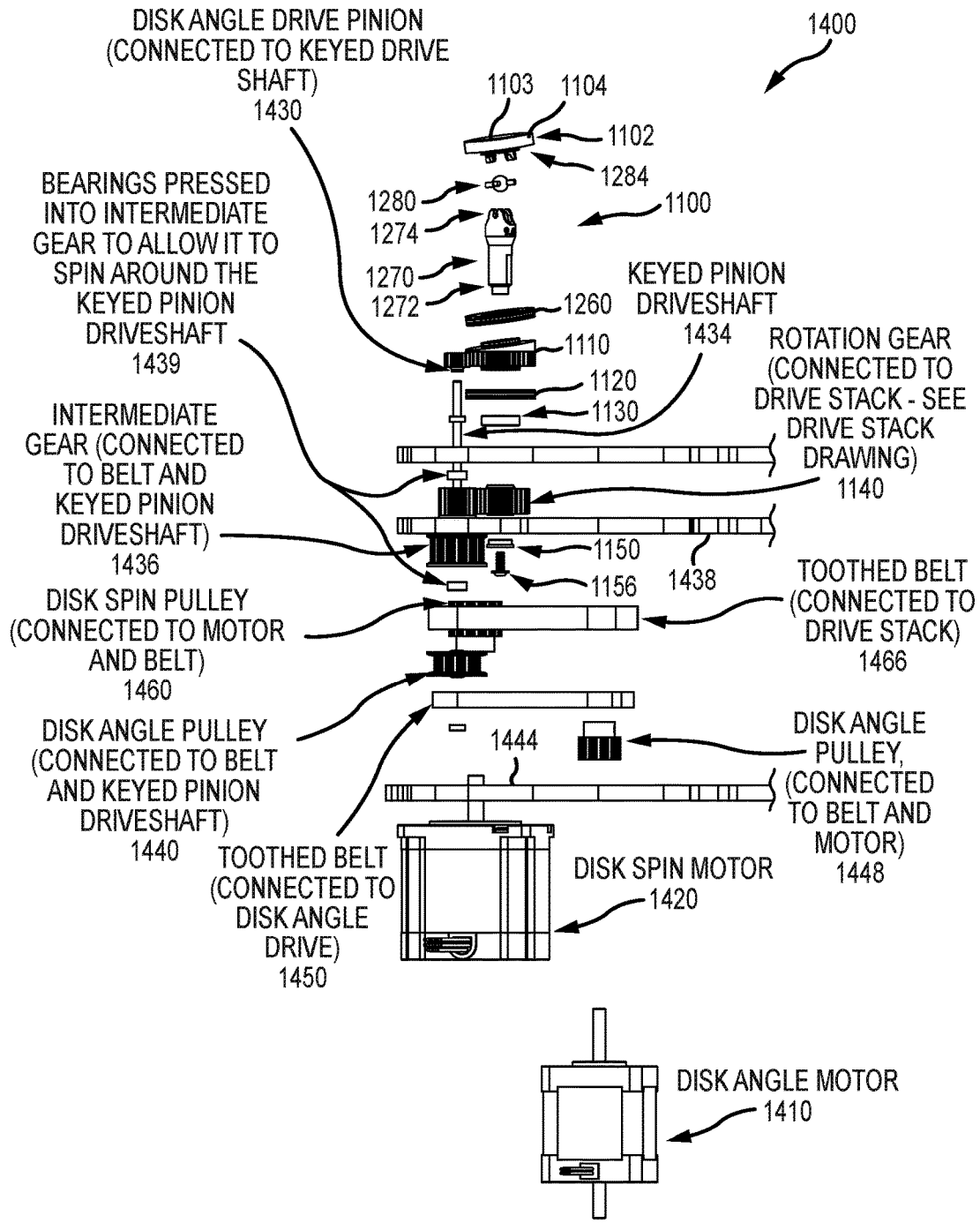
FIGS. 14 and 15 illustrate front and side views, respectfully, of another drive system for use, with the disk assembly of FIG. 12, in selectively setting the disk direction (or orienting the disk/tilt angle) and also spinning the disks about their rotation axes.
Figure 15:
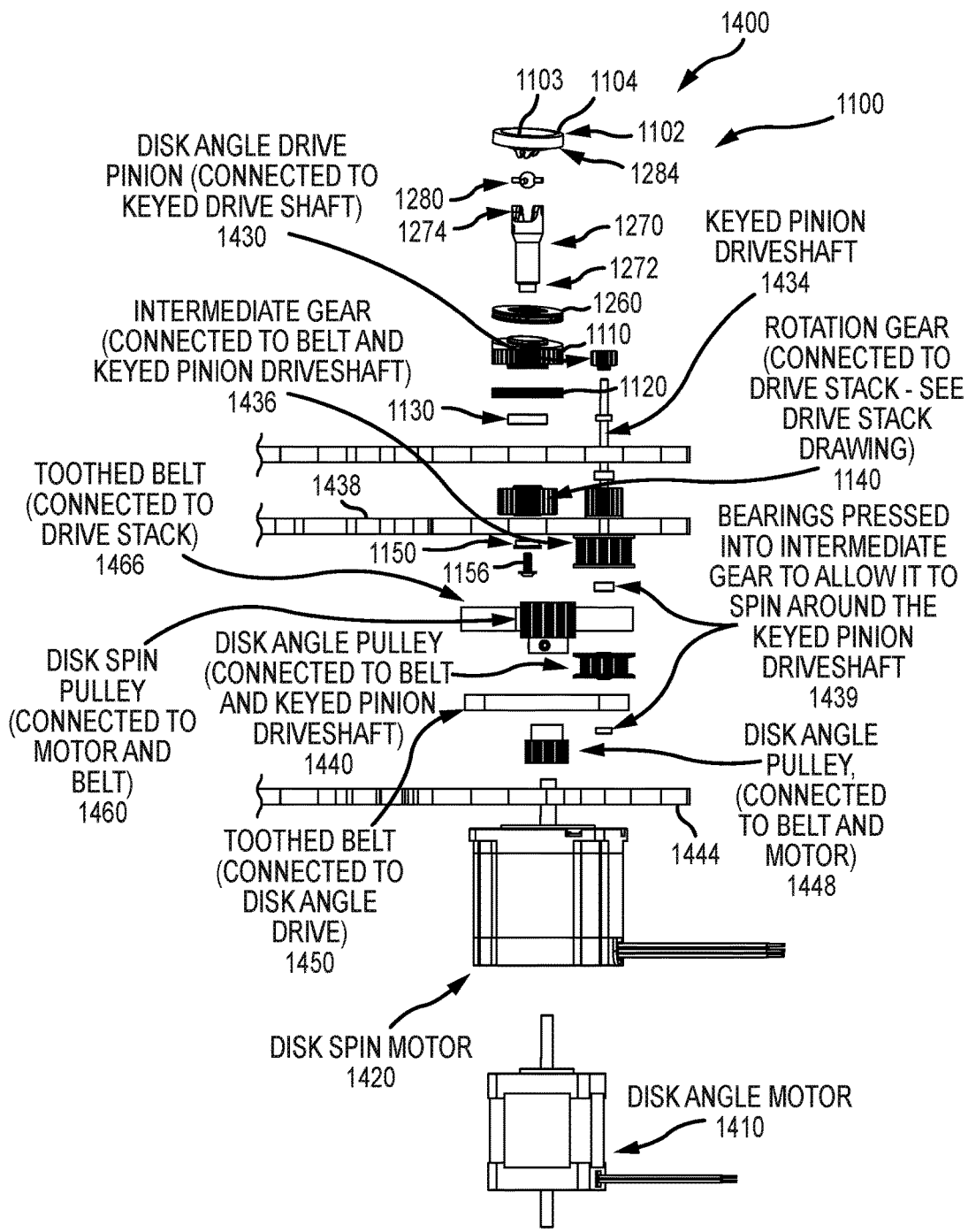

FIGS. 14 and 15 illustrate front and side views, respectfully, of another drive system 1400 for use, with the disk assembly 1100 of FIGS. 11 and 12, in selectively setting the disk direction (or orienting the disk/tilt angle) and also spinning the disks 1102 about their rotation axes. The drive system 1400 may be labeled or considered a spinning motor floor drive rather than one that utilizes worm or lead screws as shown in FIG. 13. As shown in FIGS. 14 and 15, the drive system 1400 includes a disk angle motor 1410 operable (by a tile controller or system controller) to orient the disk 1102 to place the raised edge 1104 of the disk 1102 or to set the disk direction. The drive system 1400 also includes a disk spin motor 1420 operable to cause the friction or contact disk 1102 of the assembly 1100 to rotate about its rotation axis, $Axis_{Rotation}$, with the raised portion 1104 in (and retained in) the location set by the disk angle motor 1410.

In the drive system 1400, a disk angle drive pinion 1430 is provided that is positioned to engage the gear teeth of the swashplate element 1110, and the disk angle drive pinion 1430 is connected to a keyed pinion drive shaft 1434. The keyed pinion drive shaft 1434 is coupled to an intermediate gear 1436, which is connected to a drive belt 1438, and a pair of bearings are shown that would be pressed into the intermediate gear 1436 so as to allow it to spin around the keyed pinion drive shaft 1434. The drive system 1400 further includes a disk angle pulley 1440 that is connected to the belt 1444 and also to the keyed pinion drive shaft 1434. Further, the drive system 1400 includes a toothed belt 1450 that is connected to the disk angle motor 1410 and further includes a second or lower disk angle pulley 1448 connected to the toothed belt 1450 and the disk angle motor 1410.

To spin or rotate the contact disk 1102 of the disk assembly 1100, the drive system 1400 includes a disk angle motor 1410 that is driven in response to control signals from a controller of the motion system to cause the contact disk 1102 to rotate in a desired direction and at a desired rotation rate about the disk's rotation axis. As shown, the drive system 1400 includes a disk spin pulley 1460 that is connected to the disk spin motor 1420 and also to a toothed drive belt 1466 that is connected to or engages the outer teeth of the rotation gear 1140 of the disk assembly 1100.

Figure 16:
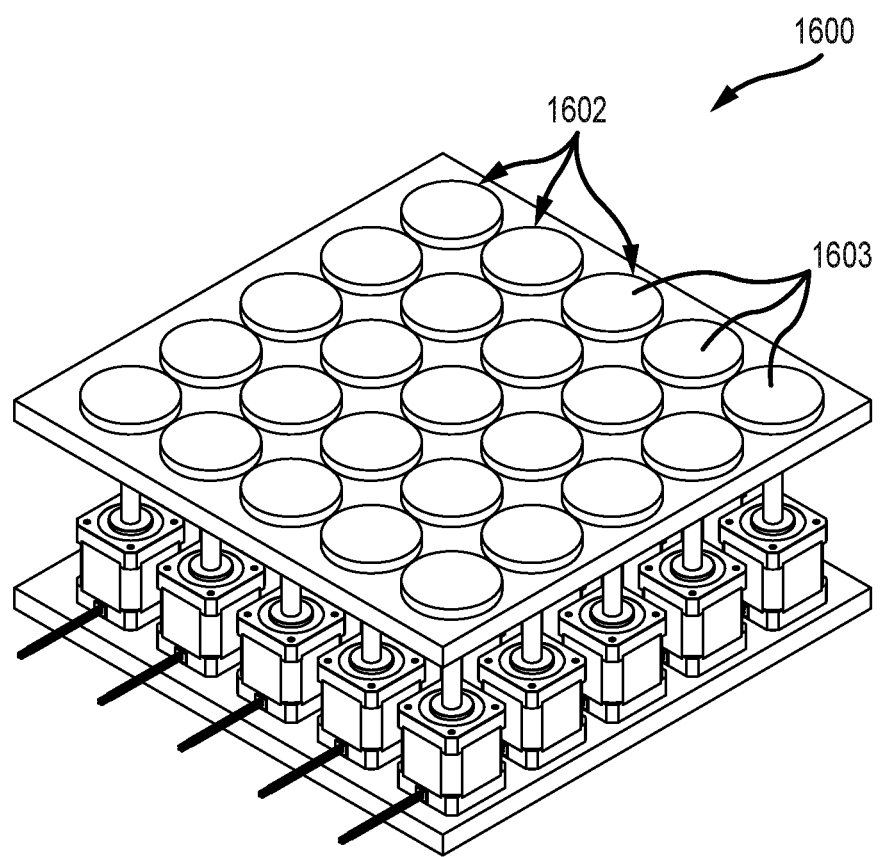
FIG. 16 illustrates a top perspective view of another embodiment of an active tile or tile assembly for use in a modular floor of a motion system of the present description.

As discussed earlier, the examples in FIGS. 11-15 are just one useful design for providing a disk assembly with a rotatable, angled disk with mechanisms for rotating/spinning the disk and for orienting the disk to have its raised edge/portion in a desired location to direct a supported object in a desired direction during disk rotation. FIG. 16 illustrates a top perspective view of another useful active tile (or tile assembly) 1600 that may be used in a modular floor of a motion system to move a supported object (e.g., a VR participant's shoe) in a desired direction and at a desired rate.

As shown, the active tile 1600 includes an upper support surface provided by the upper surfaces 1603 of a plurality or array of friction or contact disks 1602. Due to the configuration of the disk assemblies (element 1700 in FIG. 17) of which these disks 1602 are a part, the disks 1602 can be rotated about their central or rotation axis and can also be tilted at a tilt or disk angle such that only a section of the outer ring of the upper surface 1603 of the disk 1602 acts as a receiving or contact surface for the disk 1602. By choosing the orientation of the disk or direction of the disk, the raised portion can be set to move a supported object in any desired direction.

Figure 17:
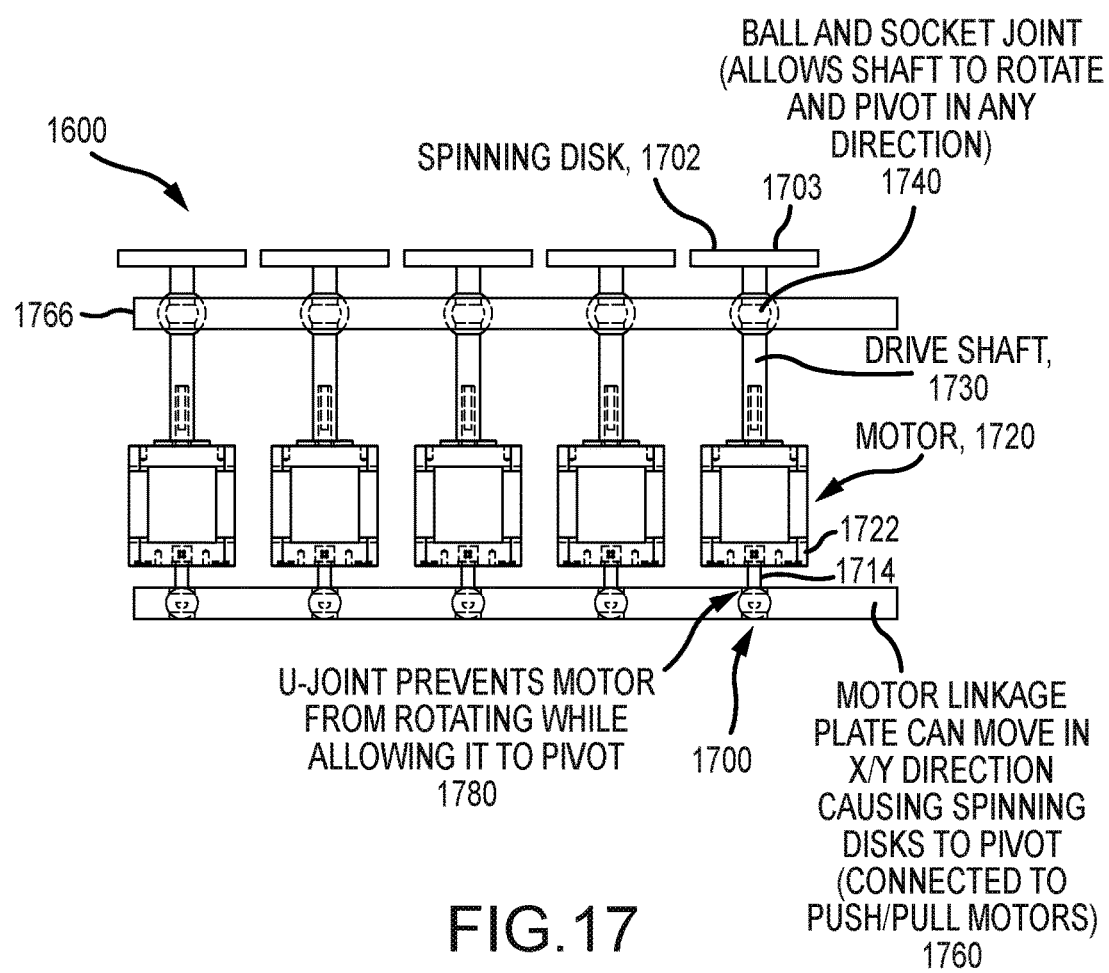
FIGS. 17 and 18 illustrate side views of the active tile of FIG. 16 in two operating states.

FIG. 17 illustrates the active tile 1600 with the disk assemblies in an at-rest or beginning position with the spinable or rotatable disks oriented with their upper contact surfaces parallel to horizontal (or prior to being tilted at a tilt/disk angle in the range of 15 to 60 degrees or more). The active tile 1600 is shown to include a lower motor linkage plate 1760 as well as an upper support plate or frame 1766, which each pivotally supports a portion of each of an array of or plurality of disk assemblies 1700. Each disk assembly 1700 includes a lower U-joint 1780 in the lower motor linkage plate 1760, with a shaft 1714 extending upward to a lower portion or base 1722 of a drive motor 1720 (i.e., the shaft 1714 supports the motor 1720 on the U-joint 1780). The U-joint 1780 is included to prevent the motor 1720 from rotation while allowing it to pivot at its lower support point (i.e., the motor 1720 is pivotally mounted to the motor linkage plate 1760).

Figure 18:
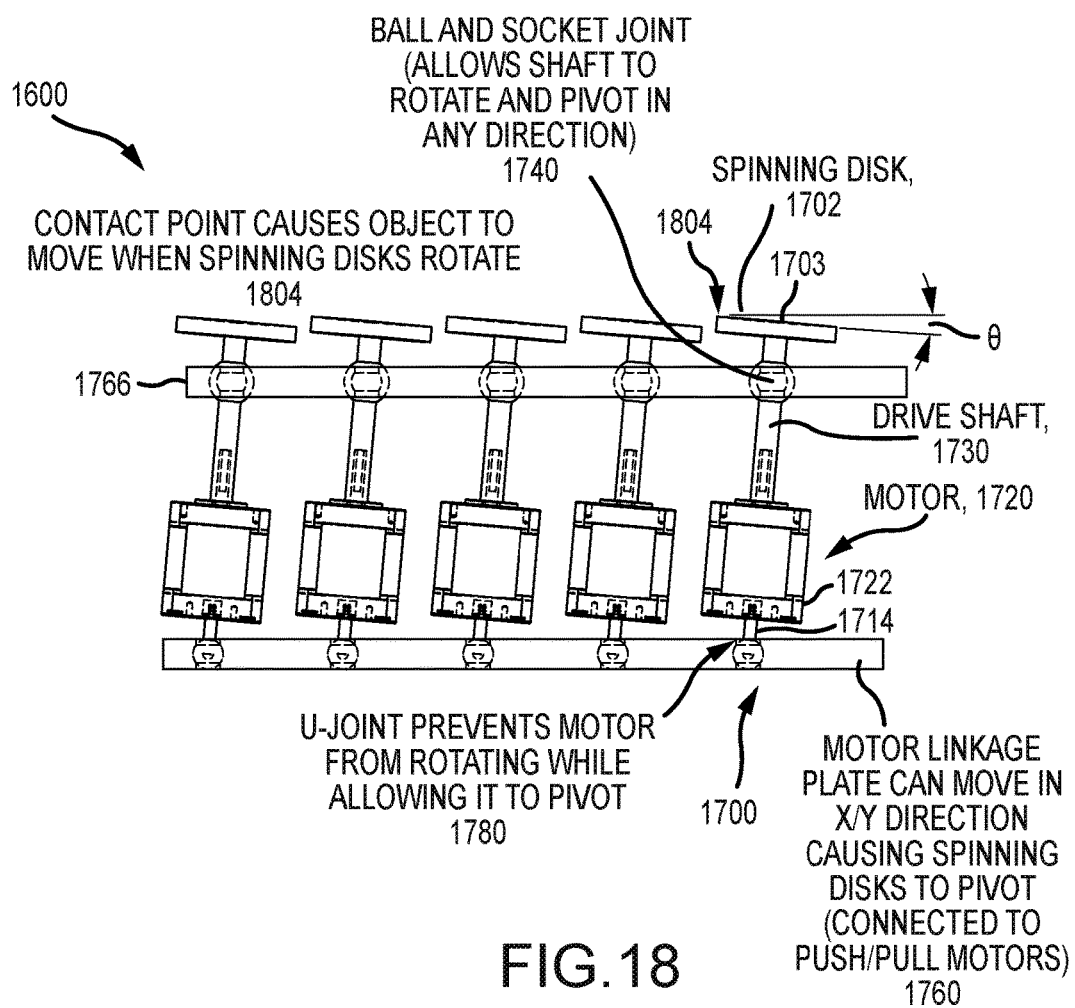

In a modular floor, the motor linkage plate 1760 is connected, for example, to push/pull motors that are selectively operated to move the plate 1760 in X-Y directions (in plane of plate) while the upper support plate 1766 is held in one position. This causes each disk 1702 in each disk assembly 1700 to be tilted to a tilt/disk angle as can be seen in FIG. 18 (with the upper support plate 1766 remaining in place or being stationary). The directional movement of the motor linkage plate 1760 not only sets the tilt/disk angle but also concurrently sets the location of the raised edge/portion 1804 of the contact surface 1703 of each contact disk 1702 so to define which direction a supported object is moved upon rotation of the disks 1702. To this end, each disk assembly 1700 includes a drive shaft 1730 extending outward from the motor 1720, and operation of the motor 1720 causes the shaft 1730 to rotate about its central axis (or the rotation axis of the disk assembly 1700 including the disk 1702). A ball and socket joint 1740 at/in the upper support plate 1766 allows the drive shaft 1730 to rotate and pivot in any direction. The outer end of the drive shaft 1730 is coupled to the contact disk 1702 (rigidly coupled to inner/lower surface of the disk 1702) such that rotation of the drive shaft 1730 by the motor 1720 causes the disk 1702 to also rotate about the rotation axis (typically, the disk's central axis). The raised contact area or point 1804 on the upper surface 1703 of the disk 1702 abuts/contacts a received/supported object and the raised portion's location causes the object to move in a controller-selectable or particular direction (e.g., along an X-axis or a Y-axis of the active tile 1600 or at any angle between these axes in either direction) when the disks rotate.

Figure 19:
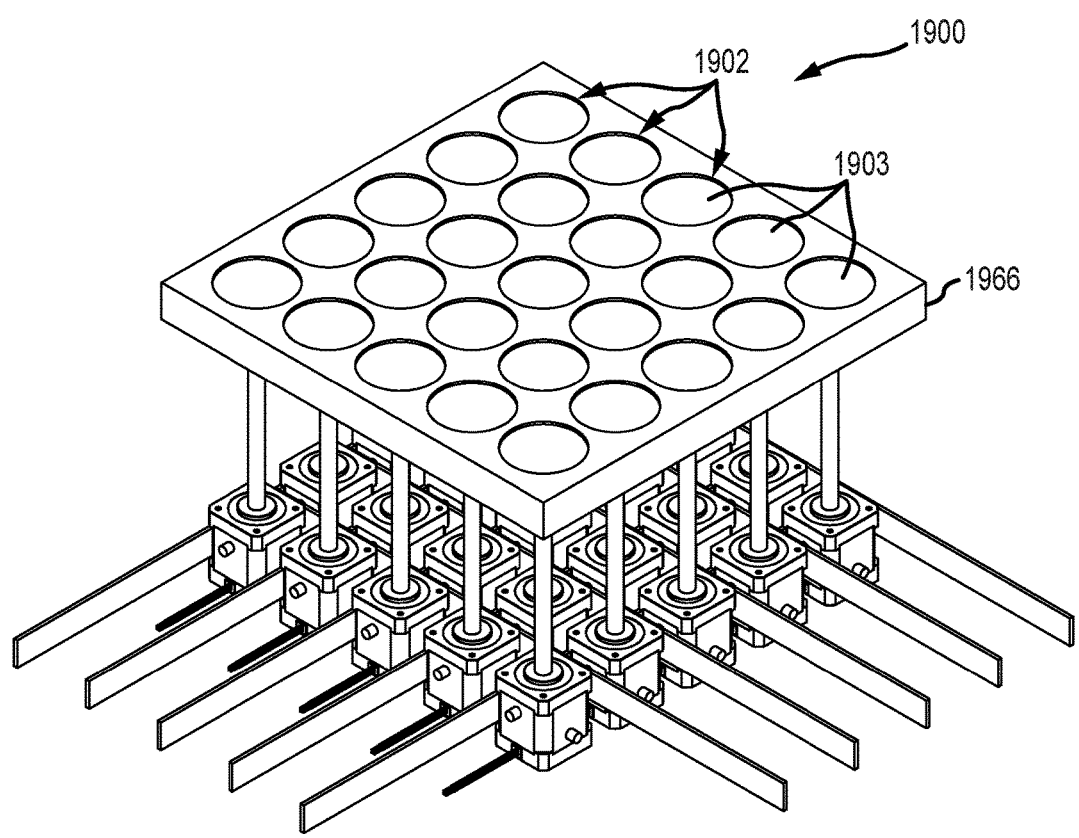
FIG. 19 illustrates a top perspective view of an additional embodiment of an active tile or tile assembly for use in a modular floor of a motion system of the present description.
Figure 20:
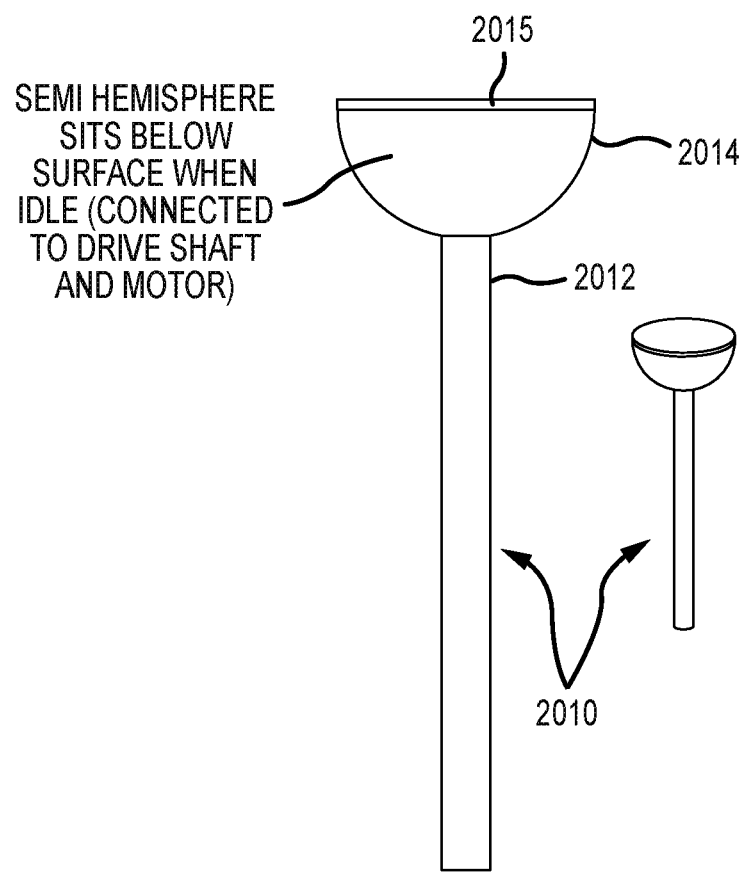
FIG. 20 is a side and perspective view of a portion of a disk assembly of the active tile of FIG. 19 showing a hemispherical-shaped disk attached to a drive shaft.

FIG. 19 illustrates a top perspective view of another embodiment of an active tile (or tile assembly) 1900 that may be used as part of a modular floor of a motion system of the present description. The active tile 1900 is useful for illustrating that the shape of the disk 1902 may be varied to provide an upper/contact surface 1903 while still practicing the inventive concept of a raised contact edge/segment on a disk 1902, which is not limited to use of a planar circular disk. The active tile 1900 may be configured with similar components as shown for tile 1600, but, as shown in FIG. 20, the disk-drive shaft mechanism 2010 may be provided with a combination of a semi-spherical or hemispherical-shaped contact (or friction) disk 2014 affixed to the end of a drive shaft 2012 with a circular upper or contact surface 2015.

Figure 21:
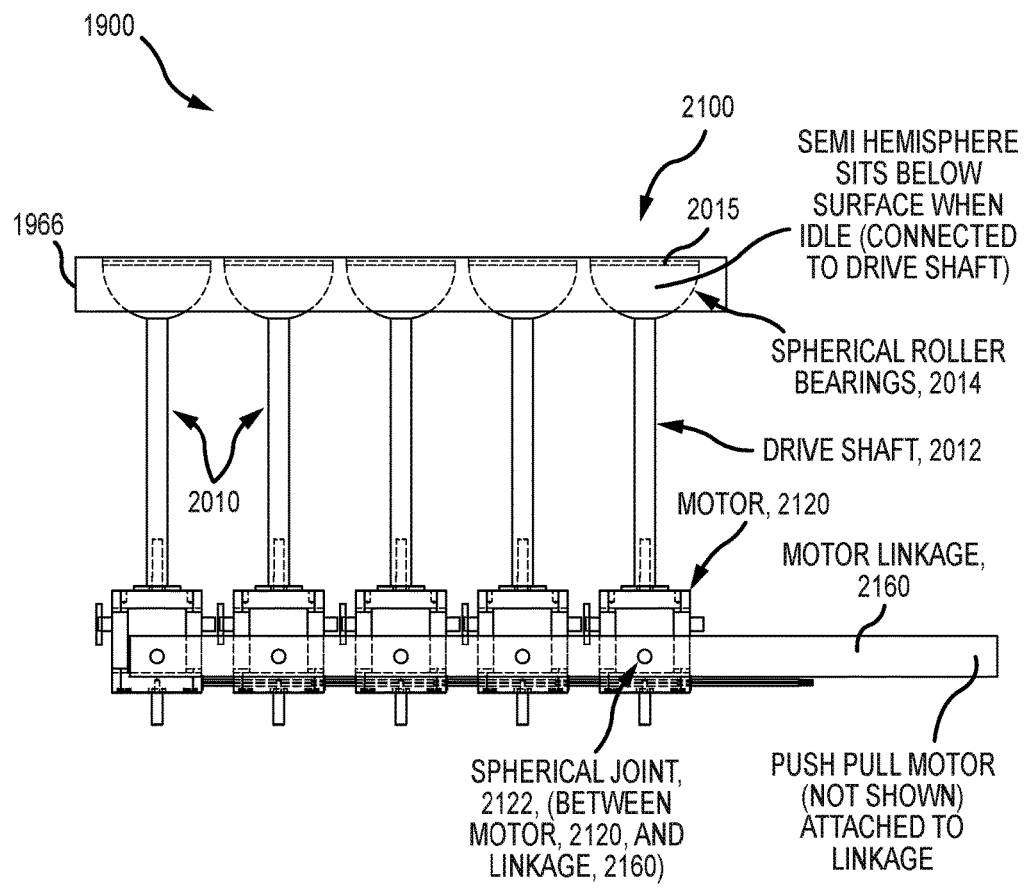
FIGS. 21 and 22 illustrate side views of the active tile of FIG. 19 in two operating states.

FIG. 21 illustrates the active tile 1900 in an initial or original operating mode/state with the semi-spherical or hemispherical shaped disk 2014 of each disk assembly 2100 positioned within the upper support plate 2166 with its upper contact surface 2015 parallel to horizontal and wholly below the upper/outer surface of the support plate 1966. As with the active tile 1600, each disk assembly 2100 includes a motor 2120 coupled to the other end of the drive shaft 2012 for selectively rotating the shaft 2012 and contact disk 2014 about the rotation axis (the central axis of the drive shaft 2012). In the active tile 1900, though, the motor 2120 of each disk assembly 2100 is directly pivotally coupled to a motor linkage 2160 (such as with a spherical joint 2122 between the motor body/housing and the linkage 2160), rather than intermediately attached via a shaft as shown in tile 1600.

Figure 22:
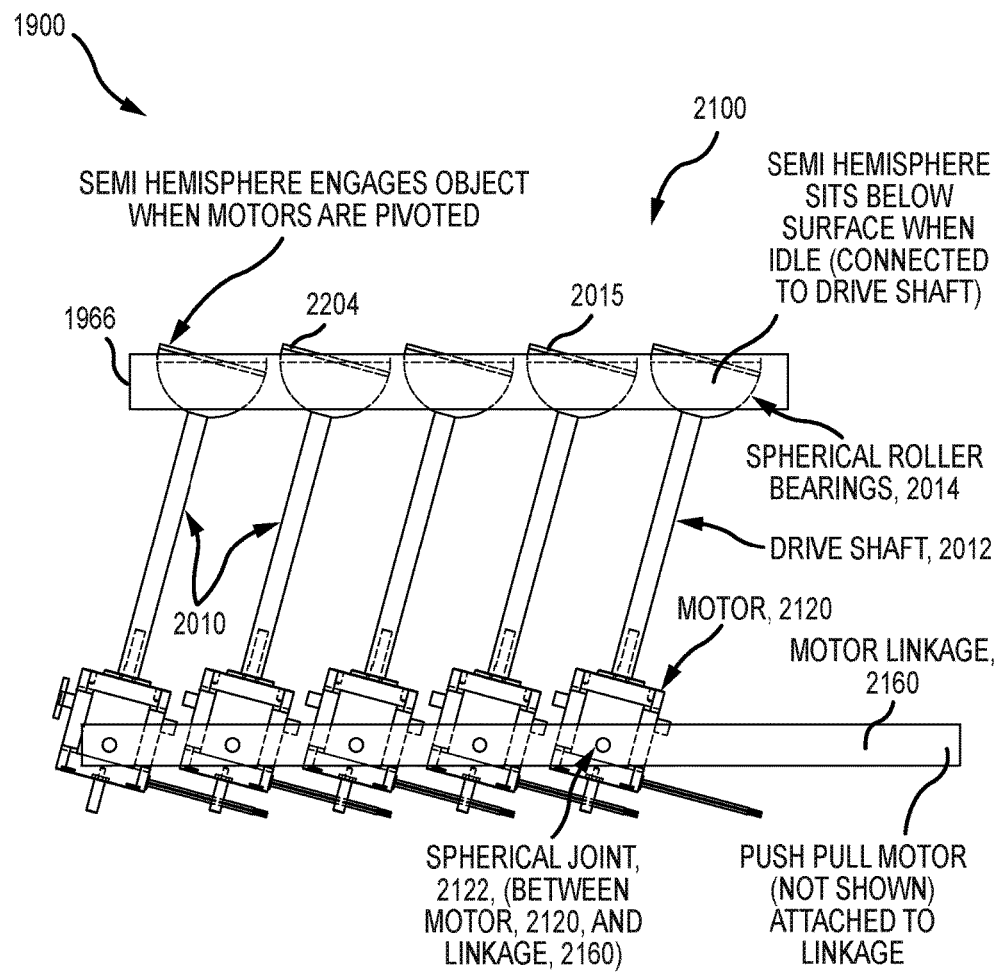

The motor linkage 2160 is attached to a push/pull motor (not shown), and this motor is used to move the linkage 2160 to pivot each of the drive motors 2120 as shown in FIG. 22, for example. Such movement of the linkage 2160 pivots each motor 2120 and interconnected drive shaft 2012 so as to also pivot each contact disk 2014, and this causes a portion or section 2204 of the contact disk 2014 to extend outward from the outer surface of the upper support plate 1966 such that these raised surfaces 2204 together act as a planar contact or support surface for the active tile 1900. An object received and supported on this set of raised edges/surfaces 2204 is moved along an X-axis, Y-axis, or in a direction between these two axes (or in X-Y coordinates) upon rotation of the friction/contact disks 2014 (with the direction being set on the disk location or how the disk is oriented to place the raised portion or edge 2204, which is achieved by selective movement of one or both of the motor linkages 2160 coupled to each motor 2120 (see, orthogonal arrangement of linkages 2160 in FIG. 19).

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

The motion system can be used in VR systems and other applications to provide infinite walking (or movement of an object) on a flat and stable surface. In the VR setting, it can provide multiple users complete freedom in choosing a walking direction. Although the motion system has moving parts, the amount of movement of any of the constituents is extremely small and vibratory in nature. Further, in some embodiments, the movement occurs at either subsonic or ultrasonic frequencies so that the moving system as a whole is quiet and should be essentially maintenance free.

Other applications for the motion system may include moving, multi-directional sidewalks (e.g., moving walkways at airports or the like). The motion system, of course, may be used to move objects other than people. For instance, the motion system may be used to move objects such as cargo and luggage at an airport, and, in some cases, the motion system could also be used to sort the objects and route it to different destinations within the facility under computer/software control.

In some cases, the motion system may utilize only the shoes/footwear taught herein (e.g., no moving floor tiles) to achieve useful results. For example, variable friction of two persons standing on the same surface. In one case, the variable friction is used to provide a more equal tug of war between two people of different size by providing less friction for the larger of the two people. In another case, variable friction is used when two people are trying to push against each other (e.g., a Sumo wrestling-type experience where the friction between one or both of the contestants and the floor may be modified/controlled). Likewise, a preferential friction may be provided on a large object (e.g., a boulder) so one or more persons can move the large object while another may not or may only be able to during particular times during a game/competition. The preferential friction shoes can be used to provide variable friction when a person is climbing upon an inclined surface.

The motion imparted upon a VR participant may involve turning the person and not always be a linear path. For example, each shoe may be independently phased and, as a result, turns can be accomplished especially when a person's left (or right) shoe is moved at a different speed than the person's right (or left) shoe. On a particular active tile, different transducers may be used to move the person's feet at different rates. The motion system may be implemented using a wide variety of friction control methods including the ones discussed above and the following approaches: (a) subsonic, audible, or ultrasonic vibration of a surface by use of piezo electric transducers; (b) transducers under a cover sheet; (c) transducers mounted on studs; (d) transducers that radiate their power through a medium such as water to a top surface that the object is positioned upon; (e) a sheet of water or other liquid that is forced under pressure through small holes in a surface based on actuation of a small "compression" cylinder (e.g., when the water has lifted the object above it, the water slides into return channel to be reused during the lift phase); (f) friction modulated by a magnetic slurry placed on the surface; (g) electromagnets to attract the shoe to the surface of the tile/plate (which could be a ferrous metal); (h) a rapid chemical reaction that either solidifies a coating material or makes it more slippery; (i) rapid state change of materials caused by rapid changes of temperature of a liquid on the surface of a tile/plate; and (j) blowing compressed or pressurized air alternately in a controlled manner through holes in the floor's (or in the tiles') upper surface (or even through holes in the lower surface of the participant's shoes/footwear).

As can be seen from the above description, floor systems are taught that may include an array of rotating, disk-shaped elements with an upper contact surface (e.g., a flat, domed, conical, truncated conical, or other shaped/contoured upper surface of a disk) that can be brought into contact with an object (e.g., a human user's shoe sole, a VR or theatrical prop, or the like) by tilting the contact disks in the array either independently or jointly as a set (such as those in an active tile in a modular VR floor). The array of disks is built into a planar flooring unit in some embodiments, and, because the disks can act independently, the floor can be built in a modular manner if desired.

In the described motion systems, the speed of movement can be controlled by varying the rotational velocity of the disks. The direction of movement is controlled by the direction of tilt of the disks supporting a particular object, with some embodiments allowing two or more objects/VR participants to be supported concurrently and moved independently in the same or different directions at the same or differing speeds. Thus, by varying both speed and tilt, the motion system can impart omnidirectional movement on any object (e.g., a human's shoes) resting upon or moving upon the surface. The rotation speed of the disks can be constant or varied. Power can be provided by a small local motor for each disk/disk assembly or alternatively by a ganged mechanism (e.g., a set of gears, toothed belts, and the like) to allow driving with a larger, common source. The tilting can be accomplished by a mechanism that tilts the direction of all elements of the array and, thus, requires only a single tilting "motor" or, alternatively, single disks or groups of disks can be tilted separately.

The motion systems taught herein that make use of rotating, tilted disks provide a user experience that is smooth and allows a supported person to walk in a manner that is comfortable and natural, with users in many prototypes not being able to detect the spinning disks underfoot. The motion system design can use continuously rotating elements/disks, and, thus, lowers friction, vibration, and power requirements when compared with the selective friction embodiments. The spinning disk embodiments has parts that are easily manufactured, and, due to the array nature of the motion system, each of the parts is similar to other parts and is amenable to mass replication. The motion system can be constructed in either a modular manner (as in individual active tiles) or can be a single larger installation with numerous disk assemblies. In some embodiments, the motion system can be adapted to allow varying speed and direction of motion of sub-portions of the mechanism allowing faster or slower movement of an object or person on portions of its surface (or through local differential movement or speeds of parts of the moved object to rotate the object). Because the flooring system always maintains local static friction with a user's shoes, there is no significant issue with the floor feeling (or actually being) slippery.

In some embodiments, it may be useful to design the module floor with the disk assemblies for enhanced safety such as with a structural plate hiding the disk assemblies such as the plate 1966 shown in FIGS. 19-22 (in which the spinning disks 2014 can be recessed until tilted to extend outward a raised portion/segment 2203). In the same or other embodiments, it may also be useful to provide a contact surface including the raised portion/segment that does not spin until an object is placed upon it such as when a VR participant's shoe steps down upon one or more disk assemblies on a VR motion floor.

Figure 23:
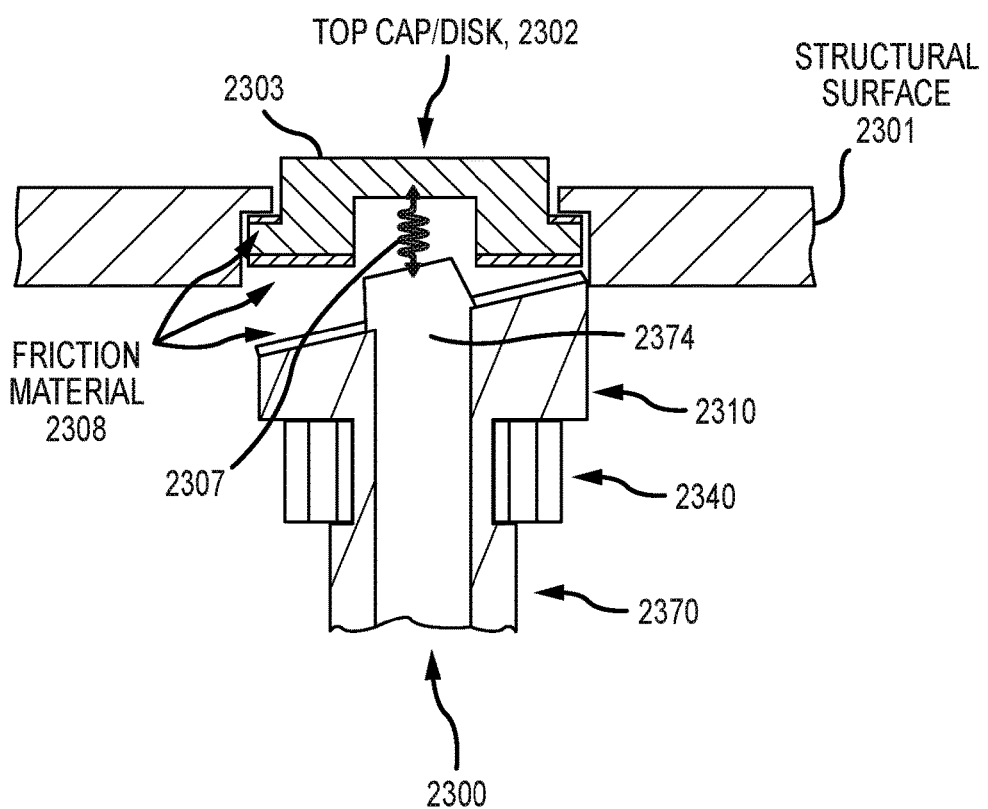
FIG. 23 is a partial view of a disk assembly of an embodiment in which a disk and its contact/upper surface only rotates/spins when a load is applied to the disk assembly.

FIG. 23 provides a portion of a disk assembly 2300 that can be used in a VR floor with such a spin-when-contacted design. As shown, a disk assembly 2300 includes a top cap or contact disk 2302 that is positioned within a recess or hole of a structural plate 2301 with an upper or contact surface 2303 extending above the upper surface of the structural plate 2301. A portion of the contact surface 2303 may mate (with friction material (or a gasket) 2308) with a lower lip of the structural plate 2301 in this hole/recess so that there are no or only small gaps to the hidden array of disk assemblies (with only one shown for ease of explanation). The top cap/disk 2302 is spaced apart a distance via a spring element (or other space) 2307 from the swashplate 2310, which used to set a tilt angle for the surface 2303 when the cap/disk 2302 is placed under a load (adequate to overcome the spring force provided by spring element/space 2307) such as when an object is placed on the disk assembly 2300.

The disk assembly 2300 further includes a rotation gear 2340 that is rotated by a driven gear (not shown in FIG. 23 but understood from prior descriptions) to cause drive shaft 2370 and interconnected shear pin 2374 to rotate about the central axis or rotation axis of the shaft 2370. Hence, when an object pressed down upon the cap/disk 2302, the contact surface 2303 is pressed against the upper surface of the swashplate 2310 and provides a raised portion/segment due to the tilt angle of the swashplate 2310, and the disk/cap 2302 rotates with the shaft 2370 and shear pin 2374 that mates with an inner/lower surface of the top cap/disk 2302.

Figure 24:
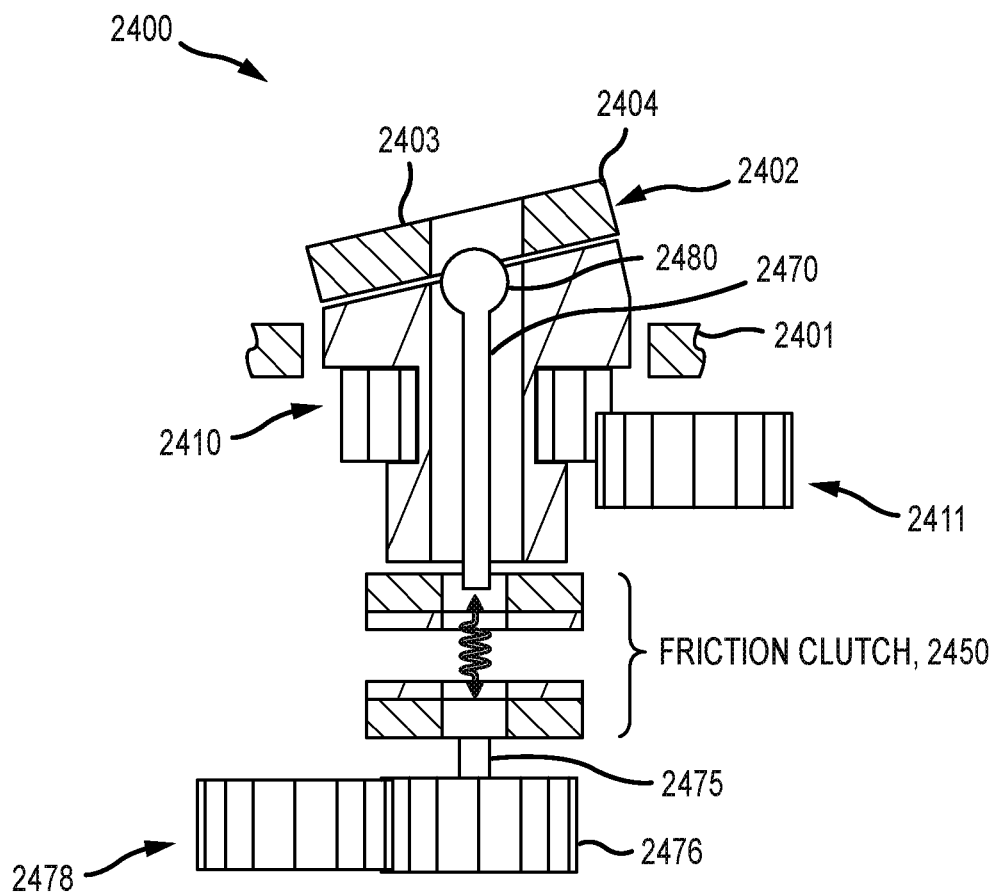
FIG. 24 is a partial view similar to FIG. 23 showing another embodiment of a disk assembly in which the disk only spins when the disk assembly is under a load or is supporting an object.

FIG. 24 illustrates another disk assembly 2400 that may be used to provide a contact surface with a raised portion/segment that only is rotating/spinning when it is used to support an object (such as a VR participant's shoe). In the disk assembly 2400, a contact disk 2402 is shown to extend outward from a hole/recess in a structural plate 2401. The disk 2402 has an exposed upper/contact surface 2403 with a raised portion or segment 2404 due to a tilt angle defined by an upper surface of a swashplate 2410 supporting the disk 2402. A drive gear or pinion 2411 is provided that when rotated sets the tilt angle of the disk 2402 by rotating the swashplate 2410. A U-joint drive 2480 is used to pivotally couple the lower surface of the disk 2402 with a drive shaft 2470 extending through the center of the swashplate 2410 to rotate the disk 2402 about a rotation axis of the assembly 2400 (e.g., a central axis of the shaft 2470).

The shaft 2470, though, only rotates when a load is applied upon the contact surface 2403 (e.g., upon the raised portion/segment 2404) that closes a small gap provided by a friction (or other type of) clutch 2450. When the clutch 2450 is engaged, rotation of a lower drive shaft 2475 is imparted through the clutch 2450 to drive shaft 2470 to the disk 2402. The lower drive shaft 2475 is coupled to a rotation gear 2476, which is rotated via a drive gear (or belt in some case) 2478 at a rate that defines the rotation rate of the disk surface 2403 and raised portion/segment 2404 to move a supported object.

In some embodiments, the disks are spinning but are recessed in holes or recesses of a structural plate. In this case, though, the structural plate is compressible or has compressible portions proximate to each disk location. When an object is placed on outer surface of the compressible floor, the compliant material of the floor allows contact with the "sunken" and rotating disk to cause the object to move with the rotating disk. Alternatively, this compressible structural plate may be combined with the embodiments shown in FIGS. 23 and 24 (e.g., the plates 2301 and 2401 may be implemented using one or more sheets of compliant and/or compressible material and may have upper/outer surfaces above that of the contact surfaces of the contact disks when not yet under a load from an object).

Figure 25:
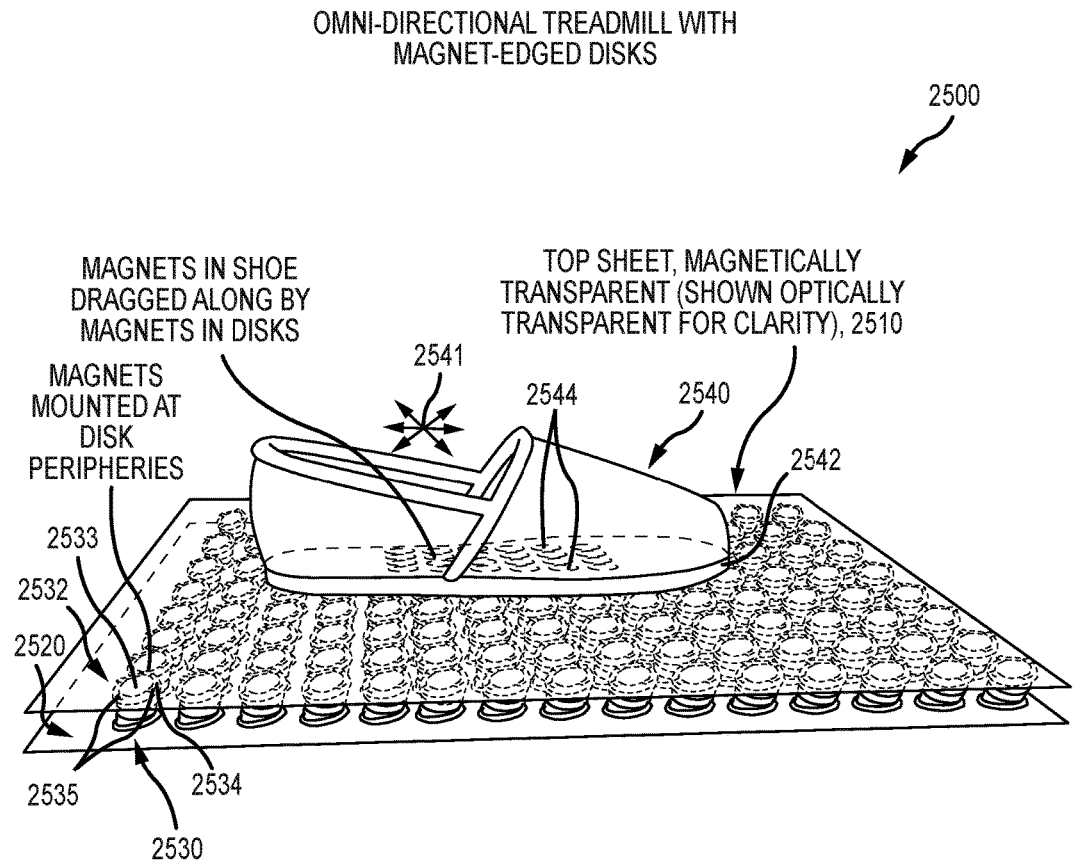
FIG. 25 illustrates a floor system 2500 that may be used in a motion system of the present description that is configured to provide a completely sealed top surface.

FIG. 25 illustrates a floor assembly 2500 that may be used in a motion system of the present description (such as for VR floor 140 of system 100 in FIG. 1), and the floor assembly 2500 is adapted to provide a completely sealed upper or top surface. To this end, the assembly 2500 includes an upper film or sheet 2510 of material that is magnetically transparent (such as a plastic sheet). An object 2540 (such as a human's shoe) is supported on the upper/outer surface of the top sheet 2510, and the object 2540 includes a base/sole 2542 with embedded ferrous elements or magnets 2544. During operation of the assembly 2500, the magnets/ferrous elements 2542 are pushed/dragged along with rotating disks at a rate set by the disk rotation rate and at a speed set by rotation rates of the disks as discussed above.

The assembly 2500 includes an array (or plurality) 2520 of disk assemblies 2530. The disk orienting and rotating mechanisms may be implemented as discussed for prior embodiments in the disk assembly 2530. The assembly 2530 differs though in that it includes a disk 2532 with an upper or contact surface 2533 with one-to-many magnets 2535, which may be positioned in the outer ring or on the periphery of the disk's contact surface 2533. As a result, the magnets 2535 are rotated through the raised portion or segment 2534 and magnetically couple or interact with the magnets/ferrous elements 2544 in the shoe/object 2540 to cause it to move 2541 in a direction set by the tilt angle of the surface 2533 and the rotation direction of the disk 2532 in the disk assembly 2530.

From the above description, it will be understood that a wide variety of drive designs may be used to orient the disks (defined tilt angles) and to rotate the disks about their rotation axes. For example, a lever arm may be used to control all of the swashplates to set tilt angles while a screw drive(s) rotates disks. In one proposed VR floor design, an "inch-worm" drive is used where disks only move a fraction of a rotation (e.g., 90 degrees total). In such a design, either every other disk moves vertically up and down to take a share of the moving weight or the floor and disks take overall turns on moving up and down. In other inch-worm designs, every disk can either free wheel or drive, and the disks are either in the drive mode or free wheel to allow a drive disk to reset. Note, nearly any of the disk assembly designs taught herein may be used in a VR floor in which they are covered with a cover such as an overall surface elastomer or the like to eliminate or reduce the possibility of small object engagement within the drive assemblies. In yet another embodiment, hydraulic plenums are provided between the structural plates used to support or tilt the disk assemblies.

Figure 26:
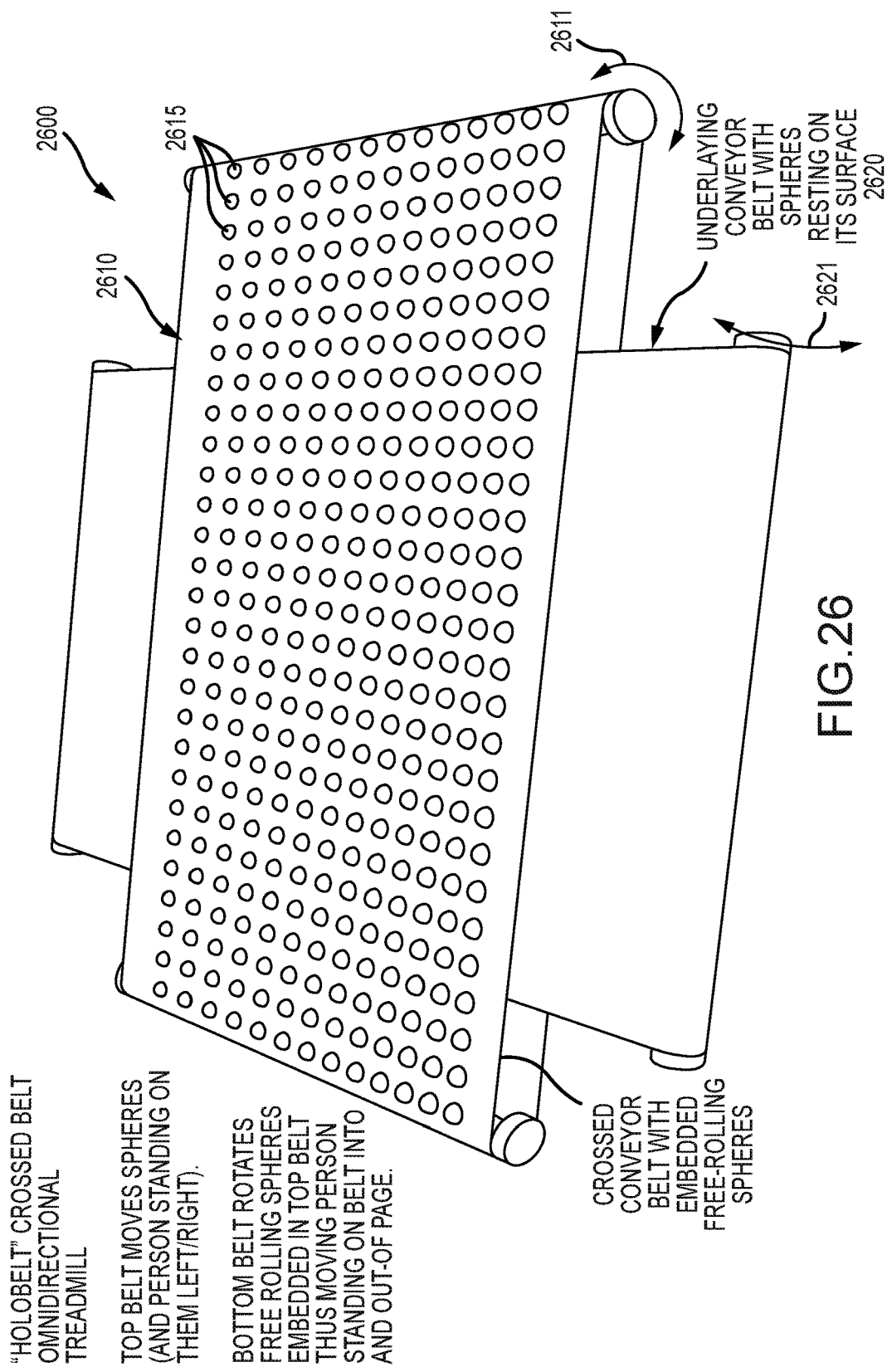
FIG. 26 illustrates a crossed belt omnidirectional treadmill embodiment of the VR floor.

FIG. 26 illustrates another floor assembly 2600 that may be used in a motion system of the present description to provide omnidirectional movement of a support object, and the assembly 2600 may be labeled a crossed-belt omnidirectional treadmill. The assembly 2600 includes an upper or crossed (or "first") conveyor belt 2610 that is selectively rotated in one of two directions as shown with arrows 2611 while an underlaying or second conveyor belt 2620 that crosses (e.g., is orthogonal as shown or at least transverse to the travel path of the belt 2610) underneath the first belt 2610 is also rotated in one of two directions as shown with arrows 2621. The upper or first belt 2610 includes a plurality of embedded spheres 2615 that are supported in the belt to be retained in place but allowed to free roll and with the bottom surfaces of the spheres 2615 resting upon the lower/second belt 2621. Hence, rotation 2611 of the first/upper belt 2610 causes a supported object to move to the left or right of the page (along the longitudinal axis of the belt 2610) while rotation 2621 of the second/lower belt 2620 causes the supported object to move, by causing rotation of the spheres 2615, into and out of the page (along the longitudinal axis of the belt 2620). Combinations of the rotations 2611 and 2621 can be utilized to cause the supported object to have omnidirectional movement.

Figure 27:
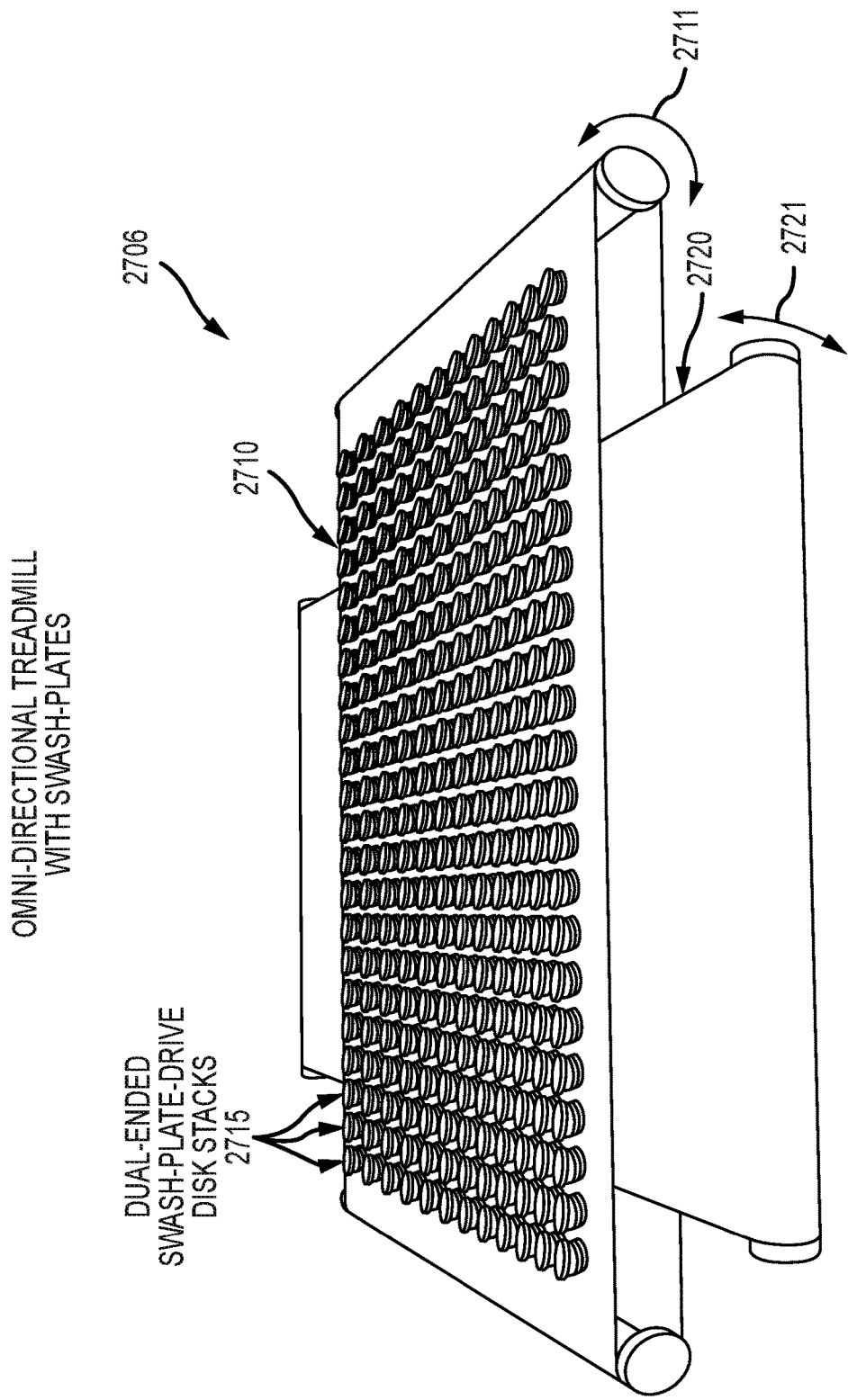
FIG. 27 illustrates a omnidirectional treadmill embodiment similar to that of FIG. 26 with disk stacks replacing the freewheeling spheres in the upper belt.

FIG. 27 illustrates an omnidirectional treadmill 2700 similar to the embodiment 2600 of FIG. 26 with disk stacks 2715 replacing the freewheeling spheres in the upper belt. Particularly, an upper or first belt 2710 is included in the treadmill 2700 that is rotatable as shown with arrows 2711 and a lower or second belt 2720 is included that is rotatable as shown with arrows 2721. The belts 2710 and 2720 may be orthogonal to each other or may otherwise be transverse at nearly any orientation with regard to each other. Each of the disk stacks 2715 is interconnected or coupled with the lower or second belt 2720 such that rotation 2721 either orients the disk to change the location of the raised portion or causes the disk of stacks over the belt 2720 to rotate at a particular speed and direction. In this manner, control over the rate and direction of the two belt rotations 2711 and 2721 can be used to impart omnidirectional movement to an object supported on a plurality of the raised portions/segments of the disk stacks 2715.

Figure 28:
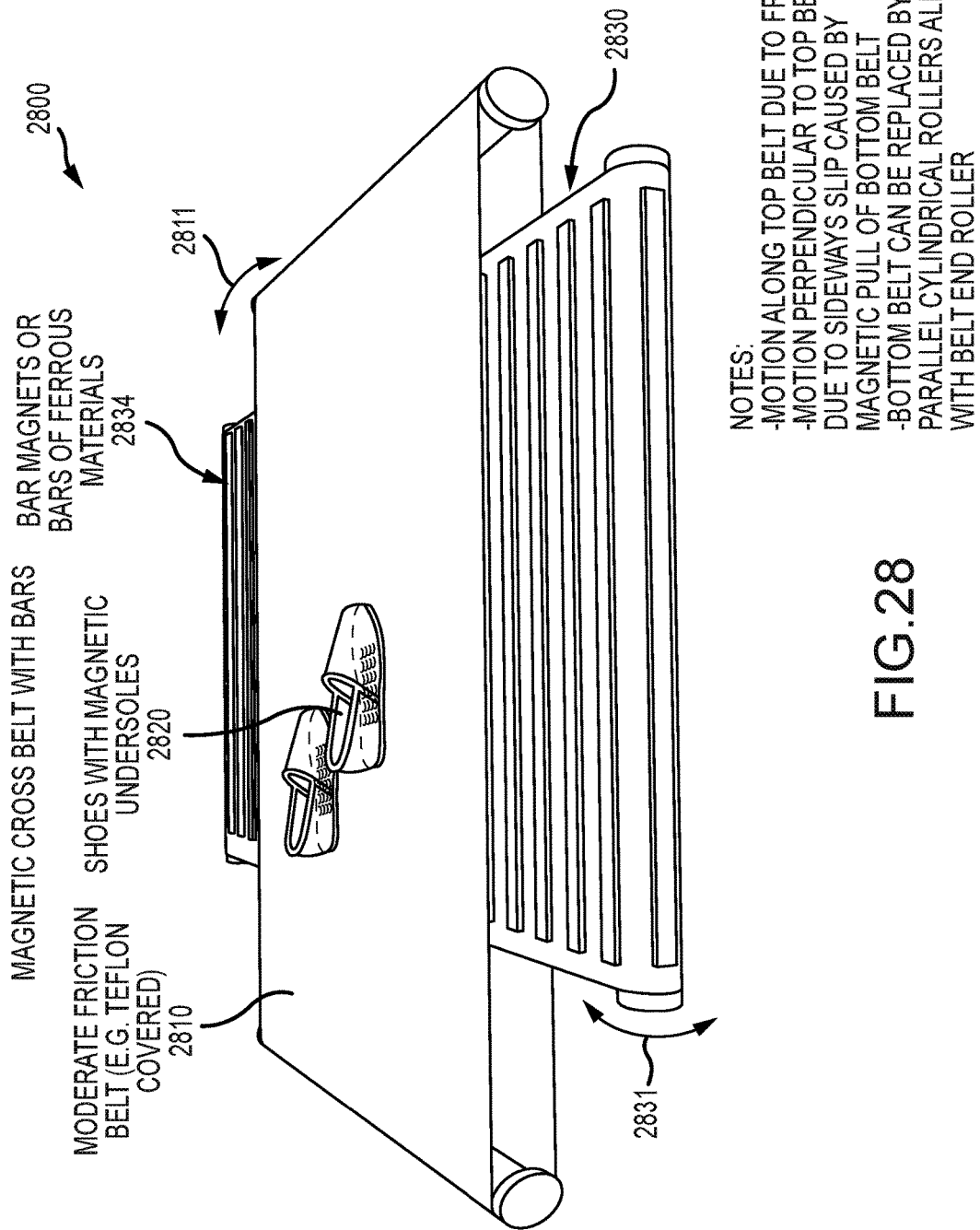
FIG. 28 illustrates a magnetic cross belt design for use in or as a floor in a motion system of the present description.

FIG. 28 illustrates a magnetic cross belt assembly 2800 that may be used in or as the floor of some motion systems of the present description to provide directional and selective movement of supported objects. The assembly 2800 includes an upper or first belt 2810 that is selectively rotated as shown with arrows 2811 to cause the belt 2810 to move in one of two directions along its longitudinal axis. The upper or first belt 2810 may be fabricated to have a lower or moderate friction outer/exposed surface that comes into contact with and supports objects 2820 such as a person's shoes that have a magnetic base (or sole or undersole when the objects are shoes). For example, the belt 2810 may be coated with or covered with Teflon or similar non-stick to lower-stick material.

The assembly 2800 also includes a second or lower belt 2830 that is selectively rotated to move in one of two directions and is arranged to have its travel path (longitudinal axis) orthogonal to the first belt 2810 or to be transverse (e.g., at an angle differing from 90 degrees). The lower belt 2830 includes a plurality of spaced apart and embedded bar magnets, bars of ferrous materials, and/or rows of magnets 2834 extending across its surface (e.g., orthogonal to the belt's longitudinal axis). During operations/use, movement of the objects 2820 is achieved due to friction along the top belt 2810. Motion perpendicular (or transverse) to the top belt 2810 is due to sideways slip caused by magnetic pull of the bar magnets or ferrous material rows 2834 in the bottom belt 2830. In some embodiments, the bottom belt 2830 is replaced with parallel cylindrical rollers aligned with belt end roller(s) of the top belt 2810.

Figure 29:
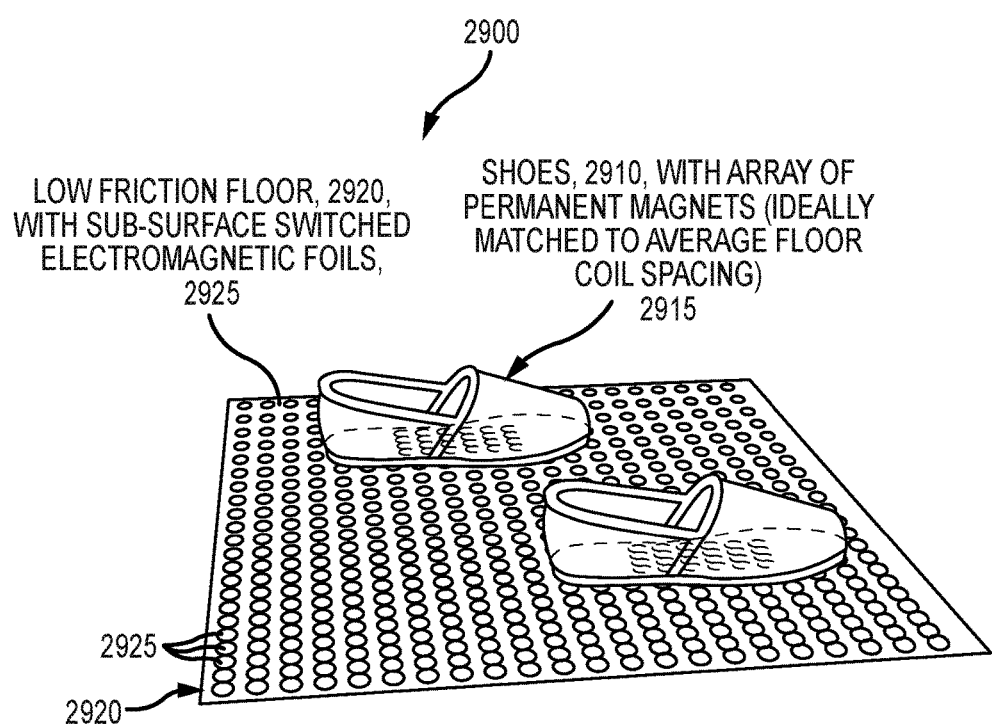
FIG. 29 illustrates a floor for use in some embodiments of a motion system utilizing magnetic stepper shoes (or objects with magnetic bases)

FIG. 29 illustrates yet another embodiment of a floor assembly 2900 that may be used as a VR floor or other floor of a motion system of the present description. In the assembly 2900, the supported objects 2910 again may include a base/sole with an array of permanent magnets 2915. For example, the objects 2910 may take the form of shoes that can be worn by a VR participant or other user of a motion system, and the shoes 2910 may include an array 2915 of permanent magnets (e.g., that may be arranged to have spacing that is matched to an average floor coil spacing). The assembly 2900 further includes a floor/support sheet 2920 that is formed of materials or a coating to provide a lower friction support surface for mating with the sole/base of the object 2910. Embedded in the floor/support sheet 2920, e.g., at some predefined distance below the contact surface of the floor 2920, is an array or plurality of spaced apart switched electromagnetic coils 2925. Selective switching of these coils 2925 on and off can be used to magnetically interact with the magnets 2915 to cause movement of the objects 2910 in nearly any direction on the floor 2920.

Figure 30:
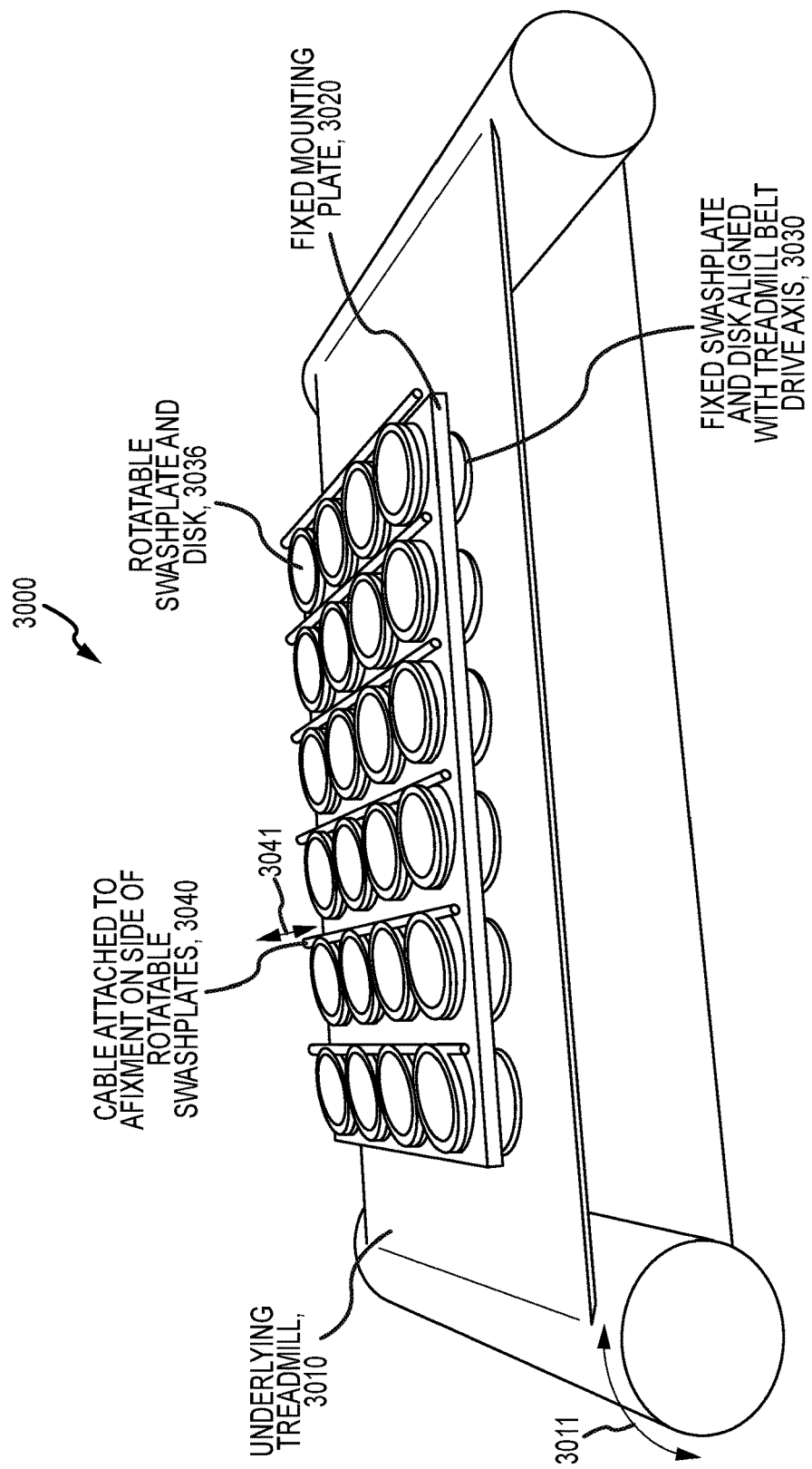
FIG. 30 illustrates an additional treadmill embodiment of a VR floor for use in a motion system.

FIG. 30 illustrates an additional treadmill embodiment of a VR floor assembly 3000 for use in a motion system, with a single tile shown for ease of explanation but with it being understood that the assembly 3000 typically could include numerous tiles for supporting a VR participant or be comprised of a single large assembly. The VR floor assembly 3000 is still based on use of swashplates, but it is configured to simplify the construction of larger area versions of a motion system. The assembly 3000 includes a treadmill 3010 that is operable as shown with arrows 3011 for movement in two directions (left and right in this example). The tile assembly is supported on an upper surface of the treadmill 3010, and it includes a fixed mounting plate 3020 that is coupled with fixed swashplates and disks 3030 aligned with the treadmill belt drive axis. The tile assembly also includes a plurality of rotatable swashplates and disks 3036 supported on each of the fixed swashplates and disks 303, and a number of drive cables (or belts or the like) 3040 mate with one or both edges of the rotatable swashplates 3036 such that for instance when the single cable 3040 moves in one of two directions (up and down in the figure) as shown with arrows 3041 the swashplates/disks 3036 also rotate about their rotation axes.

With regard to VR floor assembly 3000, one can imagine a conventional, (for instance store-bought) exercise treadmill. On top of its belt 3010, a metal plate 3020 can be positioned/supported, and screw-together swash-plate assemblies mounted through the plate 3020. A fixed angle swash-plate/disk 3030 is at the bottom and is permanently aligned with the direction of the underlying forward/backward motion of the treadmill and is simply used to convey rotation to the top disk. These bottom, fixed-orientation swash-plate disks 3030 are coupled via two U-Joints to top swash-plates 3036 whose direction of tilt can be rotated by thin steel cables 3040 that pull and push 3041 their edges to direct the top swashplates 3036 in up to 90 degrees of rotation. The 90 degrees of tilt rotation is sufficient (given that one modifies the underlying treadmill 3010 so that it can move 3011 both "forward" and "backward") to move an object on top of the rotating disks 3036 smoothly in any direction. In some embodiments, the overall weight of the swash-plate array and its mounting plate (as well as the local weight of a person standing on the plate) keeps the bottom, fixed, swash-plate-supported disks 3030 in frictional contact with the underlying treadmill belt 3010.

The plate 3020 may be anchored so that it does not move sideways or back and forth with respect to the overall treadmill 3010. Interestingly, assuming one person on the system at a time, the motor that is used to pull the cables 3040 to turn the swash-plates 30306 only has to be strong enough to primarily rotate the few swash-plates 3036 that currently have a user's foot on them (and, of course, to overcome general friction of the other swashplates). This embodiment in its simplest form uses only two motors: the treadmill motor and a second motor that could vary the rotation of tilt of all of the variable swash-plates. In this simplest form, the system 3000 does not allow multiple persons to move independently at any speed and direction, but it simplifies the mechanism to allow low cost implementation.

There are numerous useful applications of the motion systems described herein including those utilizing arrays of disk stacks or assemblies. For example, these may be used to allow a VR participant(s) to move about a space while they are concurrently having a VR experience. In another embodiment, though, the motion system is used to provide a theatrical floor rather than a VR floor. In this application, an operator may use the controller of the motion system to move an object such as an actor across a stage or allow an actor to walk as if in a larger space without reaching the boundaries/set pieces defining the theatrical space. The theatrical floor may be thought of as including an array of X-Y platform stages each capable of moving a carried/supported object to any place in, for example, a 3 foot by 3 foot planar area above the stage. Each stage could be adapted to move a powerful electromagnetic above it. In other cases, the stage may be abutted under a magnetically transparent stage floor to allow multiple performers (or props) with ferrous or magnetic soles/bases to be moved in any direction across the stage floor.

In other applications, the motion system with its flooring may be used to make better or more efficient use of stationary infrastructure. For example, motion capture, blue screen, and video tracking environments often are set up with relatively small "capture zones" in which a participant such as an actor must remain to interact with the equipment. However, there actions and activities including walking in a variety of directions that are difficult to capture in such environments as the participant/actor will quickly move out of the capture zone. For such environments, it would be very useful and desirable to provide a motion system of the present description and include a floor, such as one with active tiles described herein, to allow the participant/actor to walk and move freely while being repositioned or moved so as to stay in the capture zone.

We claim:

1. A floor system providing omnidirectional movement of a supported object, comprising:
    a plurality of disk assemblies, wherein each of the disk assemblies includes a contact disk with an upper contact surface supported at a tilt angle relative to horizontal whereby the contact disk has a raised portion for supporting an object placed on the floor system;
    a drive system comprising a disk orienting mechanism and a disk rotation mechanism for each of the disk assemblies; and
    during each operating period, a controller first operating the disk orienting mechanism for each of the disk assemblies to orient the contact disk to set a location of the raised portion and second operating the disk rotation mechanism for each of the disk assemblies to rotate the contact disk about a rotation axis at a rotation rate.

2. The floor system of claim 1, wherein the tilt angle is in the range of 5 to 60 degrees.

3. The floor system of claim 1, wherein each of the disk orienting mechanisms comprises a swashplate with an angled upper surface supporting the contact disk and wherein the swashplate is rotatable about a vertical axis to define the location of the raised portion.

4. The floor system of claim 3, wherein each of the disk rotation mechanisms comprises a drive shaft pivotally coupled at a first end to a lower surface of the contact disk and driven at a second end to rotate at the rotation rate and wherein the drive shaft extends through a center portion of the swashplate, whereby the swashplate is rotatable independent from the drive shaft.

5. The floor system of claim 4, wherein the drive system comprises a first drive assembly for concurrently rotating a plurality of the swashplates to define the location of the raised portion for an array of the disk assemblies and a second drive assembly for concurrently rotating a plurality of the drive shafts to rotate at the rotation rate in each of the disk assemblies in the array of the disk assemblies.

6. The floor system of claim 5, wherein the floor system is modular and comprises a plurality of active tiles and wherein the array of the disk assemblies is provided in one of the active tiles.

7. The floor system of claim 1, wherein the disk rotation mechanism for each of the disk assemblies comprises a motor and a drive shaft coupled to the contact disk and rotatable by the motor and wherein the disk orienting mechanism comprises a motor linkage pivotally coupled to a plurality of the motors that is operable to set an angle of the drive shafts driven by the plurality of the motors to define the tilt angle and the locations of the raised portions of the contact disks coupled to the drive shafts.

8. The floor system of claim 1, wherein the disk rotation mechanism for each of the disk assemblies is adapted to rotate the contact disk only when a load greater than a predefined minimum value is applied to the raised portion of the contact disk.

9. The floor system of claim 1, further comprising a magnetically transparent sheet covering and adjacent the contact disks, wherein each of the contact disks includes at least one permanent magnet element on the upper contact surface, and wherein the object includes one or more magnets or one or more ferrous elements in a base portion.

10. A floor system providing selective movement of a supported object, comprising:
    a plurality of active tiles each comprising a plurality of disk assemblies, wherein each of the disk assemblies includes a contact disk supported at a tilt angle whereby the contact disk has a raised portion for contacting an object; and
    a drive system for each of the active tiles, wherein the drive system of at least one of the active tiles first operates to orient the contact disks of the plurality of disk assemblies in the at least one of the active tiles to set a location of the raised portion and second operates to rotate each of the contact disks of the plurality of disk assemblies at a rotation rate about a rotation axis, wherein the rotation axes of the disk assemblies in the at least one of the active tiles are parallel.

11. The floor system of claim 10, wherein the tilt angle is fixed during rotation of the contact disk and is within the range of 5 to 60 degrees.

12. The floor system of claim 10, wherein each of the disk orienting mechanisms comprises a swashplate with an angled upper surface supporting the contact disk and wherein the swashplate is rotatable about a vertical axis to define the location of the raised portion.

13. The floor system of claim 12, wherein each of the disk rotation mechanisms comprises a drive shaft coupled to a lower surface of the contact disk and driven to rotate at the rotation rate and wherein the drive shaft extends through a center portion of the swashplate, whereby the swashplate is independently rotated relative to the drive shaft.

14. The floor system of claim 13, wherein the drive system of each of the active tiles comprises a first drive assembly for concurrently rotating the swashplates of all the drive assemblies of the active tile to define the location of the raised portion and a second drive assembly for concurrently rotating the drive shafts of all the drive assemblies of the active tile to rotate at the rotation rate.

15. The floor system of claim 10, wherein the disk rotation mechanism for each of the disk assemblies comprises a motor and a drive shaft coupled to the contact disk and rotatable by the motor and wherein the disk orienting mechanism comprises a motor linkage pivotally coupled to a plurality of the motors that is operable to set an angle of the drive shafts driven by the plurality of the motors to define the tilt angle and the locations of the raised portions of the contact disks coupled to the drive shafts.

16. A floor system providing selective movement of a supported object, comprising:
   a plurality of active tiles each comprising a plurality of disk assemblies, wherein each of the disk assemblies includes a contact disk supported at a tilt angle whereby the contact disk has a raised portion for contacting an object; and
   a drive system for each of the active tiles,
   wherein the drive system of at least one of the active tiles operates to rotate each of the contact disks of the plurality of disk assemblies at a rotation rate about a rotation axis,
   wherein the rotation axes of the disk assemblies in the at least one of the active tiles are parallel, and
   wherein the tilt angle is fixed during rotation of the contact disk and is within the range of 5 to 60 degrees.

17. The floor system of claim 16, wherein the drive system further operates to orient the contact disks of the plurality of disk assemblies in the at least one of the active tiles to set a location of the raised portion.

18. The floor system of claim 16, wherein each of the disk orienting mechanisms comprises a swashplate with an angled upper surface supporting the contact disk and wherein the swashplate is rotatable about a vertical axis to define the location of the raised portion.

19. The floor system of claim 18, wherein each of the disk rotation mechanisms comprises a drive shaft coupled to a lower surface of the contact disk and driven to rotate at the rotation rate and wherein the drive shaft extends through a center portion of the swashplate, whereby the swashplate is independently rotated relative to the drive shaft.

20. The floor system of claim 19, wherein the drive system of each of the active tiles comprises a first drive assembly for concurrently rotating the swashplates of all the drive assemblies of the active tile to define the location of the raised portion and a second drive assembly for concurrently rotating the drive shafts of all the drive assemblies of the active tile to rotate at the rotation rate.

* * * * *